United States Patent
Braunschweig et al.

(10) Patent No.: US 9,896,414 B2
(45) Date of Patent: *Feb. 20, 2018

(54) COVALENTLY PATTERNED GRAPHENE SURFACES BY A FORCE ACCELERATED CYCLOADDITION REACTION

(71) Applicant: New York University, New York, NY (US)

(72) Inventors: Adam B. Braunschweig, Miami, FL (US); Shudan Bian, Coral Gables, FL (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/243,429

(22) Filed: Aug. 22, 2016

(65) Prior Publication Data
US 2017/0044099 A1 Feb. 16, 2017

Related U.S. Application Data

(62) Division of application No. 14/417,733, filed as application No. PCT/US2013/044570 on Jun. 6, 2013, now Pat. No. 9,422,237.
(Continued)

(51) Int. Cl.
| | |
|---|---|
| *B05D 1/28* | (2006.01) |
| *C07D 209/08* | (2006.01) |
| *B82Y 30/00* | (2011.01) |
| *B82Y 40/00* | (2011.01) |
| *C07F 17/02* | (2006.01) |
| *C01B 32/194* | (2017.01) |
| *B82Y 15/00* | (2011.01) |

(52) U.S. Cl.
CPC .......... *C07D 209/08* (2013.01); *B05D 1/283* (2013.01); *B82Y 30/00* (2013.01); *B82Y 40/00* (2013.01); *C01B 32/194* (2017.08); *C07F 17/02* (2013.01); *B82Y 15/00* (2013.01); *C01B 2204/02* (2013.01); *Y10S 977/734* (2013.01); *Y10S 977/847* (2013.01); *Y10S 977/958* (2013.01)

(58) Field of Classification Search
None
See application file for complete search history.

(56) References Cited

U.S. PATENT DOCUMENTS

| | | | |
|---|---|---|---|
| 6,966,997 B1 | 11/2005 | Inganas et al. | |
| 9,422,237 B2 * | 8/2016 | Braunschweig | B82Y 30/00 |

(Continued)

FOREIGN PATENT DOCUMENTS

| | | |
|---|---|---|
| JP | 2004-535349 | 11/2004 |
| KR | 10-2011-0110538 | 10/2011 |

OTHER PUBLICATIONS

Sarkar et al., "Diels-Alder Chemistry of Graphite and Graphene: Graphene as Diene and Dienophile", JACS, vol. 133 No. 10, (Feb. 22, 2011).*

(Continued)

Primary Examiner — Lisha Jiang
(74) Attorney, Agent, or Firm — Foley & Lardner LLP

(57) ABSTRACT

The present invention relates generally to molecular printing techniques for use in sensors, assays, and integrated optics and electronics. Specifically, the present invention relates to covalent patterning of graphene surfaces.

10 Claims, 23 Drawing Sheets

SLG

Related U.S. Application Data

(60) Provisional application No. 61/677,924, filed on Jul. 31, 2012, provisional application No. 61/684,614, filed on Aug. 17, 2012.

(56) References Cited

U.S. PATENT DOCUMENTS

| | | |
|---|---|---|
| 2009/0255462 A1 | 10/2009 | Cannara et al. |
| 2010/0028559 A1 | 2/2010 | Yan et al. |
| 2010/0240922 A1 | 9/2010 | Wong et al. |

OTHER PUBLICATIONS

Menard-Moyon et al., Functionalization of Single-Wall Carbon Nanotubes by Tandem High-Pressure/Cr(CO)6 Activcation of Diels-Alder Cycloaddition, JACS, vol. 128, (2006), pp. 14764-14765.

Sarkar et al., Diels-Alder Chemistry of Graphite and Graphene: Graphene as Diene and Dienophile, Journal of the American Chemical Society, 2011, vol. 133, Feb. 22, 2011, pp. 3324-3327.

Sarkar et al., Chemistry at the Dirac Point: Diels-Alder Reactivity of Graphene, Accounts of Chemical Research, vol. 45 No. 4, (Mar. 9, 2012), pp. 673-682.

Notification of Transmittal of The International Searching Report and The Written Opinion of the International Searching Authority, or the Declaration, dated Nov. 21, 2013, 11 pages.

\* cited by examiner

FORCE

SLG

SLG

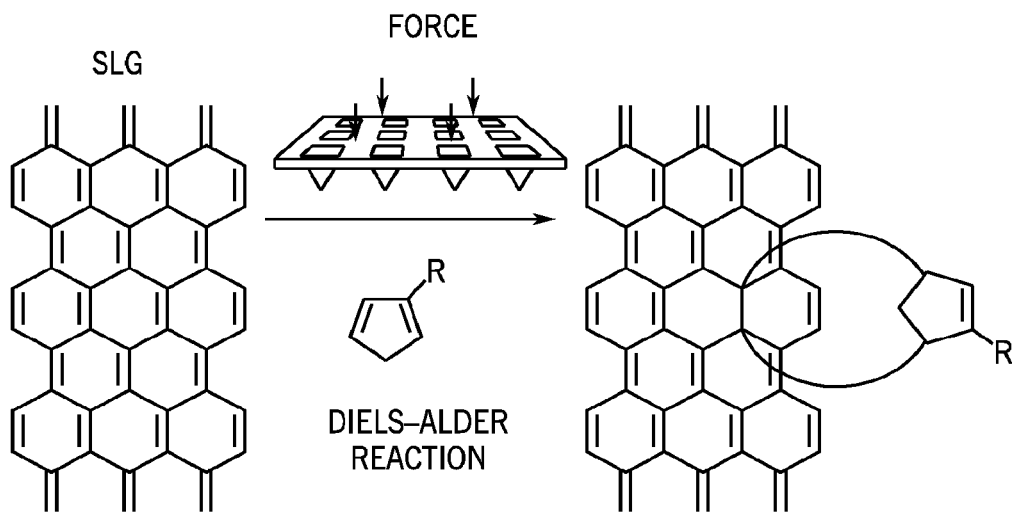
FIG. 1E
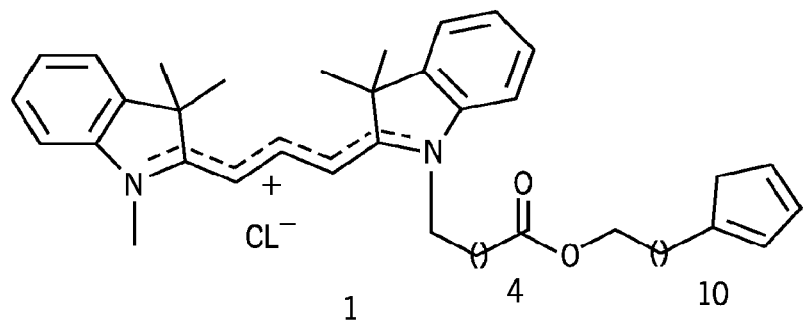
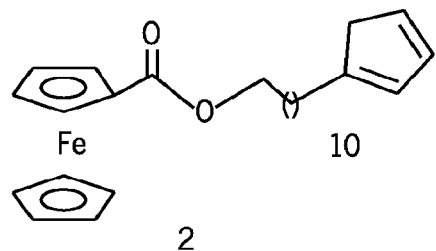
FIG. 1F

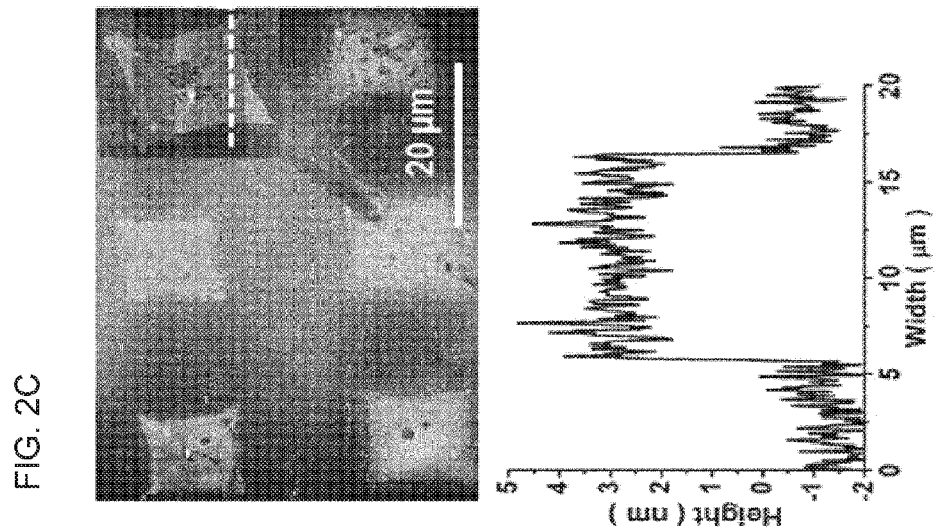
FIG. 2C
FIG. 2D
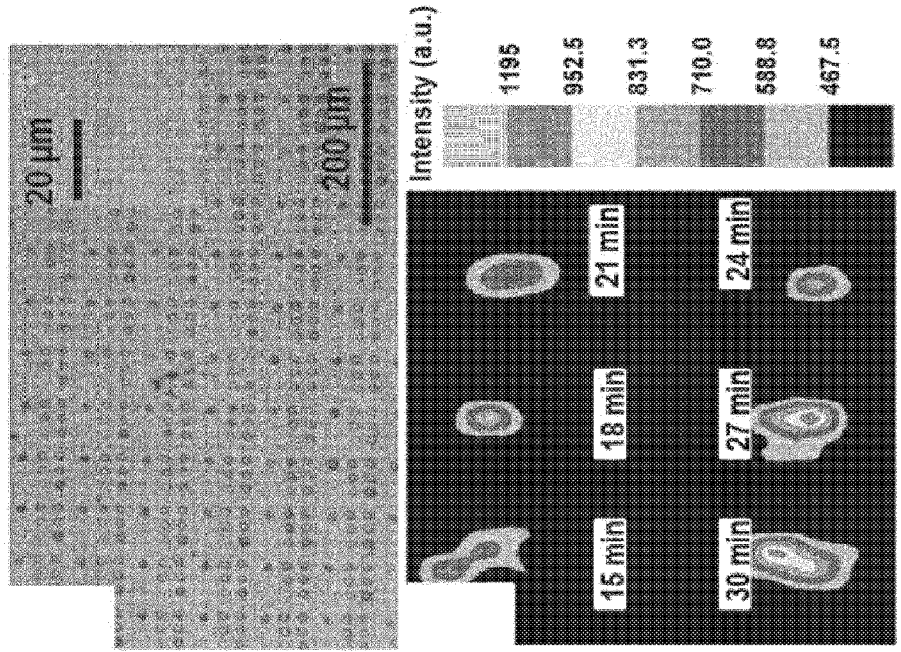
FIG. 2A
FIG. 2B

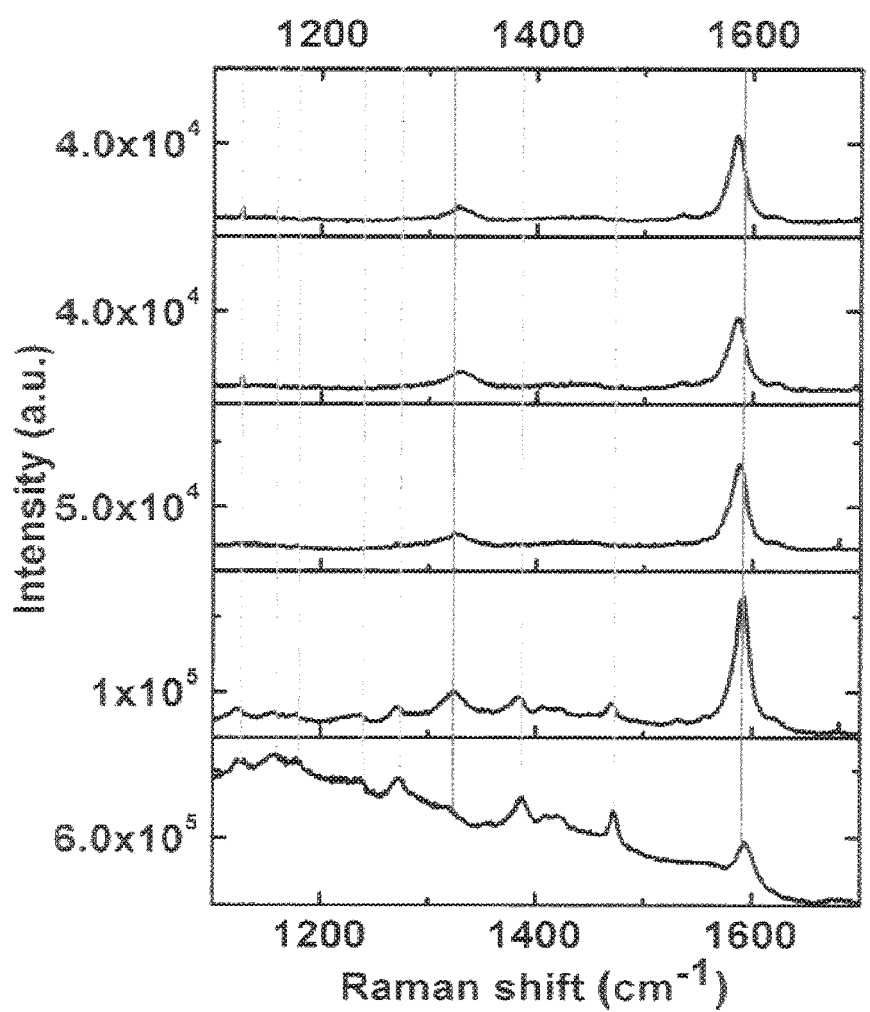

FORCE

SLG

SLG

COVALENTLY PATTERNED GRAPHENE SURFACES BY A FORCE ACCELERATED CYCLOADDITION REACTION

CROSS REFERENCE TO RELATED PATENT APPLICATIONS

The present application is a divisional application of U.S. application Ser. No. 14/417,733 (now U.S. Pat. No. 9,422, 237), filed Jan. 27, 2015, which claimed priority to U.S. Application No. 61/684,614, filed Aug. 17, 2012 and U.S. Application No. 61/677,924 filed Jul. 31, 2012. All of these applications are incorporated herein by reference in their entireties.

STATEMENT OF GOVERNMENT-SPONSORED RESEARCH

This invention was made with United States government support awarded by the following agencies: The Air Force Office of Scientific Research Young Investigator Award (FA9550-11-1-0032), and the National Science Foundation (DBI-115269, DMR-0820341 and CHE-01162222). The United States government has certain rights in the invention.

FIELD OF THE INVENTION

The present invention relates generally to molecular printing techniques for use in sensors, assays, and integrated optics and electronics. Most particularly, the present invention relates to covalent patterning of graphene surfaces using a force-accelerated reaction.

BACKGROUND OF THE INVENTION

Graphene, a carbon allotrope consisting of one atom thickness of planar sheets of $sp^2$-bonded carbon atoms, has become the focus of considerable research attention because of its high conductivity, 2D structure, and superior mechanical properties. Site-specific patterning on graphene can increase the bandgap of this material for applications in integrated optics and electronics, and the immobilization of soft organic and biologically active materials is necessary for the fabrication of graphene-based sensors. While the adaptation of conventional lithographic processing to graphene is being pursued for the fabrication of integrated electronics, many of these potential applications can only be realized through the combination of organic reactions on graphene with molecular printing techniques. However, a consequence of the stabilizing conjugation of graphene is that the basal plane is resistant to chemical functionalization, so carrying out site-specific organic reactions on graphene is challenging. Consequently, this extended conjugation provides thermal stability and resistance to chemical functionalization that would perturb the stabilizing delocalization that extends along the basal plane. For this reason, the basal plane of graphene is significantly less reactive than other fullerene carbon allotropes.

Functional molecules such as methoxide have been shown to be anchored to graphene using noncovalent interactions onto the basal plane or coupling to oxidized defect sites and edges (see FIG. 18). Alternatively, photochemical, dipolar-cycloadditions, and diazonium salt reactions are known to couple organics directly to the basal plane of graphene; however the requisite input of energy would denature or destroy soft matter, and thus such methods are not compatible with molecular patterning techniques.

There remains, therefore, a need for reliable, scalable and commercially applicable techniques for immobilization of soft organic and biologically active materials via site-specific patterning on the basal plane of graphene for use in integrated optics and electronics.

SUMMARY OF THE INVENTION

The present invention relates to surface chemistry, ink transport, and characterization techniques for covalent reactions, developed to address the problems with existing techniques outlined above. Graphene has received intense interest as an active material in sensors, electronics, and optics. The invention features described herein give rise to the ability to immobilize biological probes by force-induced patterning, while still maintaining the conductivity of the graphene substrate. This can be used, for example, to make field-effect sensors, wherein the binding to graphene is detected by changes in the electrical field around a field-effect transistor. Moreover, in sensor applications for targets such as carbohydrate binding proteins that could be markers for cancers or other diseases, the polymers that are grown off the graphene surface often have a higher binding affinity, and, as a result, have much improved detection sensitivity than their monomeric counterparts. With regards to electronic and optical applications that use graphene, one drawback of graphene is its low bandgap. Covalent modifications to the basal plane of graphene can tune the bandgap so that graphene can be used as an active material in transistors. Another consequence of increasing the bandgap is that the optical absorption can be tuned, so that graphene can be employed in photonic devices. The invention set forth herein can in fact solve these problems and achieve the desired results.

In one aspect, the present invention provides a method of covalently patterning soft matter onto the basal plane of a graphene surface, said basal plane comprising or coated with a first reactive element, said method comprising the steps of: (a) coating an elastomeric tip array of an atomic force microscope ("AFM") with an ink mixture comprising a second reactive element; (b) inducing a localized force-accelerated reaction between the first reactive element and the second reactive element by mechanical application of the elastomeric tip array to the graphene surface, resulting in a covalent bond between the first and second reactive elements; and (c) rinsing the graphene surface to remove unbound ink. In another embodiment rather than use an AFM to create a pattern, an alternate approach for covalently patterning graphene surfaces can involve elastomeric stamps used commonly in microcontact printing to exert force between the ink and the substrate. The methods described herein to apply force to achieve a desired product should not be limited to tips or even elastomeric stamps, but could include any material that could apply a suitable force. Consequently, a conventional system which can controllably apply the second reactive element can be used.

In some embodiments, the force-accelerated reaction may be a cycloaddition, which may, in further embodiments, be selected from the group consisting of the Diels-Alder reaction, a 1-3 dipolar cycloaddition, and other cycloaddition reactions, including [4+2] cycloadditions of cations and anions, cycloadditions involving more than six electrons, photochemical cycloadditions, and stepwise cycloadditions. In still further embodiments, the first reactive element may be a dienophile, such as graphene, and the second reactive element may be a diene, such as, in some embodiments, rhodamine cyclopentadiene or ferrocene cyclopentadiene. In still further embodiments, the reaction may result in a cyclohexene formation covalently bonding the first and second reactive element. The ambient temperature during manufacture may, in some embodiments, be as low as 25° C., and the reaction time may be three hours or less. In other embodiments, the ink mixture may further comprise polyethylene glycol (PEG) (see FIG. 1(B)). polytetramethylene glycol (PTMG), polytetramethylene ether glycol (PTMEG), or agarose. The soft matter may be selected from the group consisting of nanoparticles, organics, biologicals, polymers, proteins, sugars, oligonucleotides, peptides, and antibodies.

Another aspect of the present invention provides a method of selectively and locally increasing the bandgap of single layer graphene said graphene comprising or coated with a first reactive element, and said method comprising the steps of: (a) coating an elastomeric tip array with an ink mixture comprising a second reactive element consisting of or bound to a soft matter element; and (b) inducing a localized force-accelerated reaction between the first reactive element and the second reactive element by mechanical application of the elastomeric tip array to the graphene surface, resulting in a covalent bond between the first and second reactive elements; wherein the bandgap is increased in those locations on the basal plane of the graphene with functionalized, covalently immobilized molecules.

In yet another aspect, the present invention provides a sensor comprising: a graphene substrate; functionalized soft matter molecules covalently immobilized on the surface of the graphene substrate; wherein the covalent immobilization is the result of a force-accelerated Diels-Alder reaction. In some embodiments, the sensor may be used with applications that include gene chips, glycan arrays, peptide arrays, sensors, field-effect transistors, and biomimetic surfaces for fundamental biological investigations.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

As used herein, "soft matter" includes nanoparticles, organics, biologicals, polymers, proteins, sugars, oligonucleotides, peptides, antibodies, and other like components.

As used herein, "bandgap" refers to the energy range for a given solid in which no electron states can exist, calculated in electron volts as the space between the top of the valence band and the bottom of the conduction band.

As used herein, "Raman spectroscopy" refers to any spectroscopic technique used to study vibrational, rotational, and other low-frequency modes in a system that relies on inelastic scattering of monochromatic light. Generally, monochromatic light from a laser interacts with molecular vibrations, phonons or other excitations in the system, resulting in the energy of the laser photons being shifted up or down and giving information about the vibrational modes in the system. Light from the illuminated spot is collected through a lens and sent through a monochromator. Wavelengths close to the laser line due to elastic Rayleigh scattering are filtered out while and the remainder is dispersed onto a detector. Raman spectroscopy is a standard tool for characterizing chemical modifications onto the basal plane of graphene.

As used herein "Raman Mapping" refers to a method to obtain localized Raman spectra on a surface by using a microscopy to focus the laser excitation. This method provides a unique spectrum for each pixel on the surface, whose resolution is limited by the microscope optics.

As used herein, "cyclic voltammetry" refers to any method of determining electrochemical properties wherein working electrode potential is ramped linearly versus time, and wherein, once reaching a set potential, the working electrode's potential ramp is inverted, and the current is measured between the working electrode and the counter electrode.

As used herein, a "local" increase in bandgap refers to an increase limited to an area in which molecules have been immobilized onto a graphene surface.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 1(A)-1(F) illustrates tip-induced force accelerated Diels-Alder reaction on a single layer graphene (SLG) surface; FIG. 1(A) shows an elastomeric tip-array; FIG. 1(B) shows the tip-array coated with an ink mixture (red or "r") consisting of a cyclopentadiene and poly(ethylene glycol) (PEG); FIG. 1(C) shows the inked tip array pushed into the SLG surface to form a cyclohexane; FIG. 1(D) shows that, following rinsing of the surface to remove the PEG and excess cyclopentadiene, only the covalently immobilized molecules remain on the surface; FIG. 1(E) shows the Diels-Alder reaction between functionalized cyclopentadiene and an SLG surface; FIG. 1(F) shows Raman active ink molecule rhodamine cyclopentadiene (hereinafter "1") and electrochemically active ink molecule ferrocene cyclopentadiene (hereinafter "2") used to confirm force-accelerated patterning;

FIG. 2(A) is a photograph of a light microscopy image (10× magnification) of 2×3 dot arrays of a mixture containing 1 and PEG with varying dwell times (30, 27, 24, 21, 18, 15 min) patterned by each pen in the PPL tip array; scale bar is 200 μm; the inset is a magnified image of one array, with the scale bar at 20 μm; FIG. 2(B) shows the Raman mapping image (1324 $cm^{-1}$, D band) of 2×3 dot arrays of 1 covalently immobilized onto the SLG, with the scale bar at 20 μm; FIG. 2(C) shows an AFM image of a single feature printed onto the SLG and FIG. 2(D) shows a height profile of a feature of 1 patterned onto SLG;

FIG. 3(A) shows the Raman spectrum of 1 on an $SiO_2$ surface; FIG. 3(B) shows Raman spectrum taken from a map with force accelerated printing of 1 taken at a position with increased ft-band ($I_D$) and having peaks corresponding to 1; FIG. 3(C) shows the Raman spectrum from the map of the same printed surface taken at a position without $I_D$; FIG. 3(D) shows the Raman spectrum of a control experiment where PEG and force were applied to the surface without 1 at a point where the tips were pushed into the SLG surface; FIG. 3(E) shows the Raman spectrum of pure SLG;

DETAILED DESCRIPTION OF THE PREFERRED EMBODIMENTS

Figure 1A:
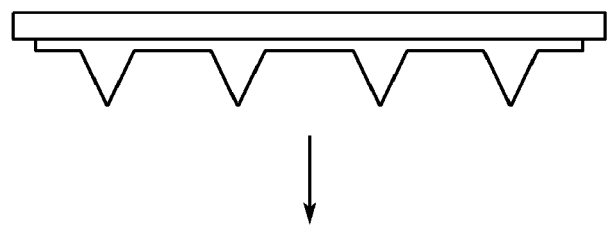
Figure 1B:
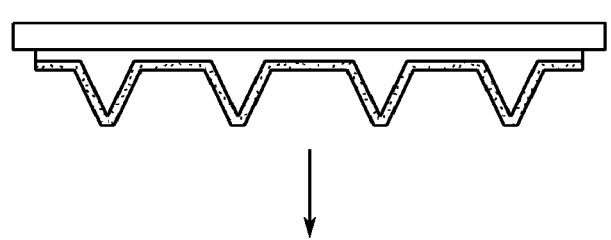
Figure 1C:
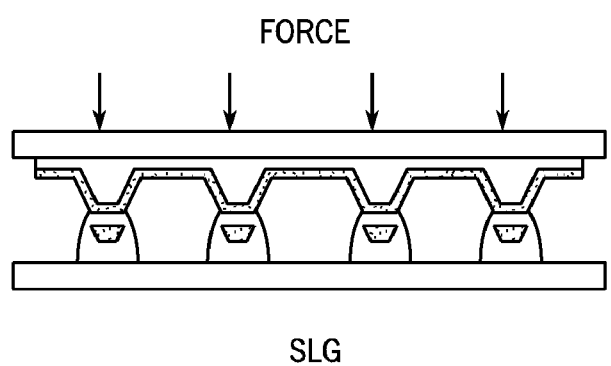
Figure 1D:
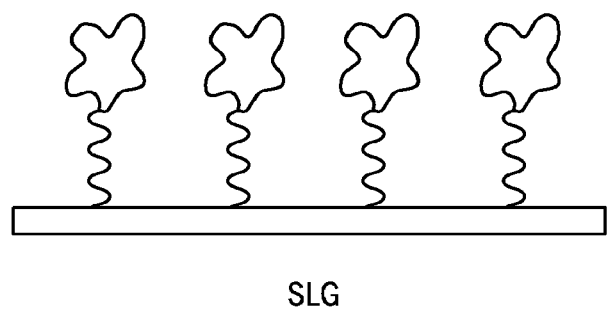

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

In one preferred embodiment shown in FIGS. 1(A)-1(F), it is illustrated that the present invention is based upon the discovery that single layer graphene (SLG) participates in Diels-Alder reactions as a dienophile (see FIG. 17) at temperatures as low as 25° C. over 3 hours. The illustrated reactions and suggested possible end product are illustrative only and do not limit or otherwise reduce the scope of the claims herein. These conditions can be used to scalably pattern graphene at ambient temperatures and atmosphere. Further, because of their negative activation volumes, cycloaddition reactions are significantly accelerated in pressurized reaction vessels, and the present invention is based on the further discovery that induction of Diels-Alder through a localized applied force allows for micropatterning of various small organic molecules. The present invention may be used with applications that include gene chips, glycan arrays, peptide arrays, sensors, and biomimetic surfaces for fundamental biological investigations.

Figure 17:
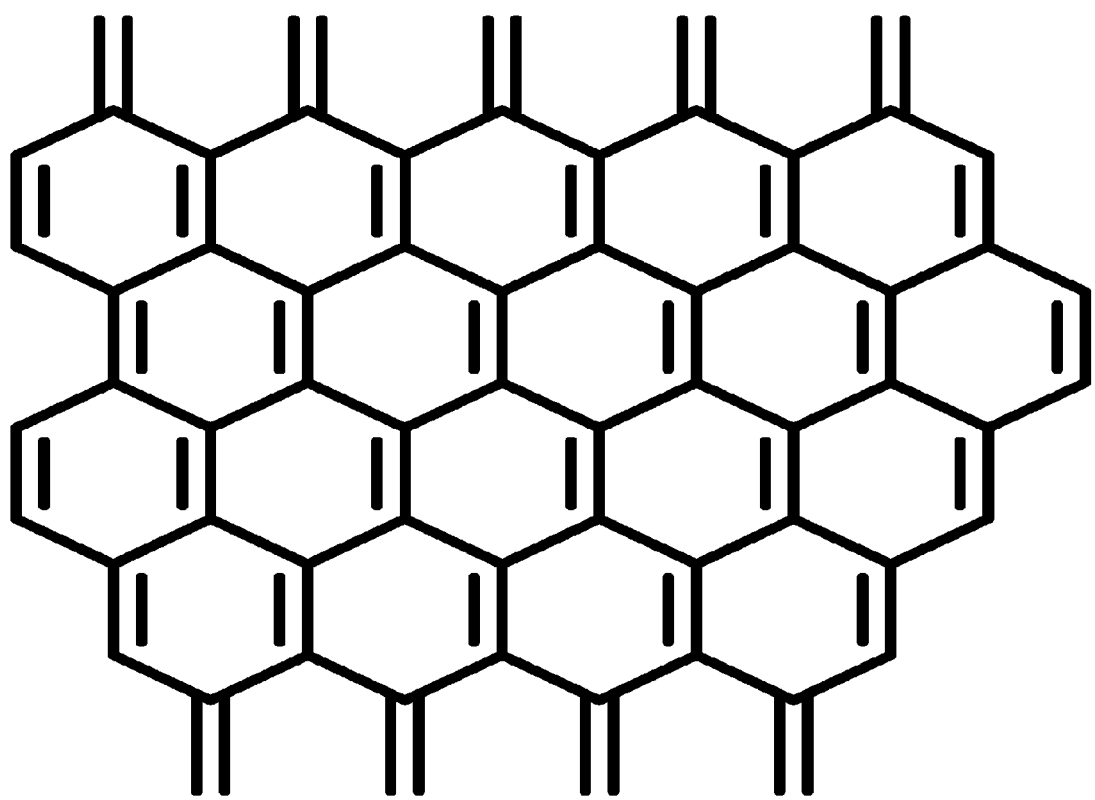
FIG. 17 shows a schematic of the structure of SLG as a dienophile.
Figure 18A:
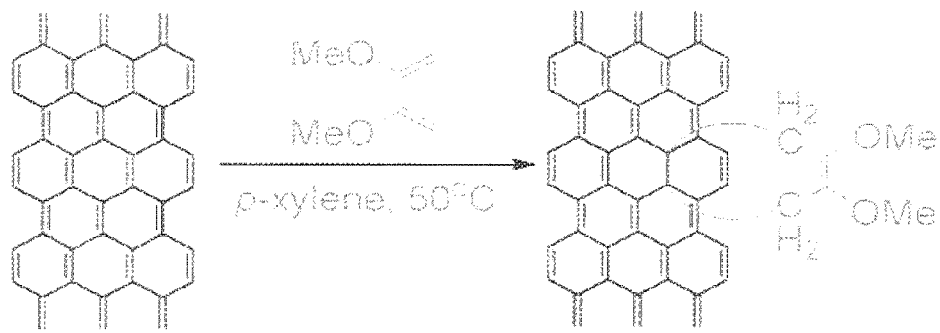
FIG. 18(A) is a schematic showing the covalent interaction between SLG and methoxide, catalyzed by para-xylene, at 50° C.; and 18b is a line graph showing the Raman shift resulting therfrom.
Figure 18B:
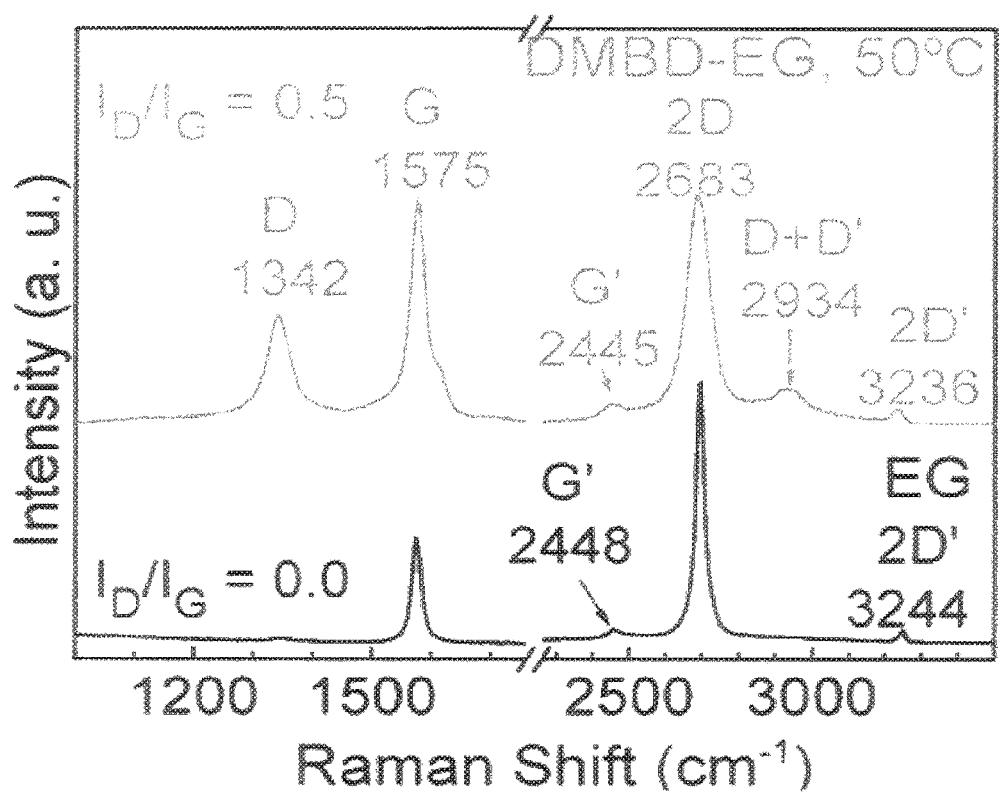

The Diels-Alder reaction is a thermal cycloaddition between a conjugated diene and a substituted alkene ("dienophile") (see FIGS. 1(E) and 17, for example) to form a substituted cyclohexene system, requiring comparatively little energy. It occurs via a single transition state, and is sped up by application of pressure. In one of the resonance forms of graphene, the delocalized pi-electrons can take the form of localized pi-bonds, which can react subsequently with dienes in the context of a Diels-Alder reaction (see FIGS. 1(A)-1(F)).

To demonstrate that force accelerated cycloadditions can covalently pattern large areas (~1 cm$^2$) of SLG sheets, an elastomeric tip array (see FIG. 1(A)) was mounted onto the piezoelectric actuators of an atomic force microscope (AFM) and was used to site-specifically apply a force between functionalized cyclopentadienes and SLG sheets. As noted hereinbefore other conventional systems, such as elastomeric stamps can be used as well as other methods and systems enabling pressure controlled chemical reactions to be implemented. These tip arrays are commonly used for Polymer Pen Lithography, where patterns are formed by ink transfer from the tips to the surface through an aqueous meniscus, resulting in a relationship between dwell time and feature size. Moreover, their large areas (>1 cm$^2$) and the computer controlled movement of the piezoactuators that hold the array provide high throughput and flexible pattern design. These arrays are suitable for covalently patterning soft matter nondestructively through selective organic transformations. Because the elastomeric tips also compress upon contact with surfaces, they can apply a predictable force between molecular inks and a surface. The relationship between applied force and the resulting feature sizes (Eq. 1), $$F = \frac{(L_f - L_c)E_2 L_t}{v} \quad \text{(Eq. 1)}$$

Where $L_f$ is feature edge length of the top of the tip, $L_t$ is the feature edge length of the bottom of the tip, $E_2$ is the compression modulus of poly(dimethyl siloxane) (PDMS), and v is the Poisson's ratio of PDMS, which can be used to determine the force between the tips and the surfaces. As a result, in this experimental design, the position, force, and time (see FIGS. 2(A)-2(D)) can all be controlled precisely to pattern surfaces with micrometer scale features over a square centimeter. Various examples of this methodology, resulting articles and characterizations thereof are shown in FIGS. 1(a)-23 and Examples provide further non-limiting illustrations of the invention.

Raman-active Cyanine 3 (Cy3) containing cyclopentadiene 1 and electrochemically-active ferrocene cyclopentadienes 3 were designed to characterize the bonding and density upon reaction between the SLG surface and the cyclopentadienes see FIGS. 1(A)-1(F) and 19(A)-19(F) showing the basic method) and postulated potential chemical reactions which are non-limiting examples. Cyclopentadienes react quickly in Diels-Aider reactions compared to open chain dienes because they are structurally preorganized for reaction; and as a result, they have been utilized already in the context of surface patterning. Raman spectroscopy has become the standard tool for characterizing chemical modifications onto the basal plane of graphene. Following a Diels-Alder reaction onto graphene, the D band at 1345 cm$^{-1}$ that corresponds to the $A_{1G}$ breathing vibration of sp$^2$ carbon rings, which is suppressed in pure graphene, increases significantly because the introduction of defects or covalently adsorbed molecules reduces the symmetry of the graphene lattice. As a result, the ratio of the D- and G-band intensities ($I_D/I_G$), measured using the integration of the peaks, is a relative measure of the degree of functionalization of graphene (see FIGS. 3(A)-3(G)). Alternatively, electrochemistry can confirm the immobilization of the ink onto the surface and quantify the density of surface-bound molecules.

SLG sheets on SiO$_2$ substrates have been patterned covalently with organic small molecules through a force-accelerated Diets-Alder (hereinafter also referenced as "DA") reaction induced by an array of pyramidal elastomeric tips (again see the basic method in FIGS. 1(A)-1(F)) and 19(A)-19(F). The changes in bonding were characterized by Raman microscopy and cyclic voltammetry, and the results were consistent with site-specific covalent modification of graphene (see FIGS. 2(A) and 2(B)). Although graphene is heralded as a promising material in various applications, the inability to pattern the surface and alter the band structure under mild conditions has slowed the realization of some applications. The method, articles and compositions of matter described herein demonstrate that graphene can be patterned covalently with micrometer scale features over large areas at room temperature and ambient atmosphere, while accessing one of the most versatile reactions in organic chemistry. By increasing the Poisson's ratio of the polymer used in the tip or reducing the force used to induce the reaction, the features edge lengths can be reduced below 1 μm.

Figure 19A:
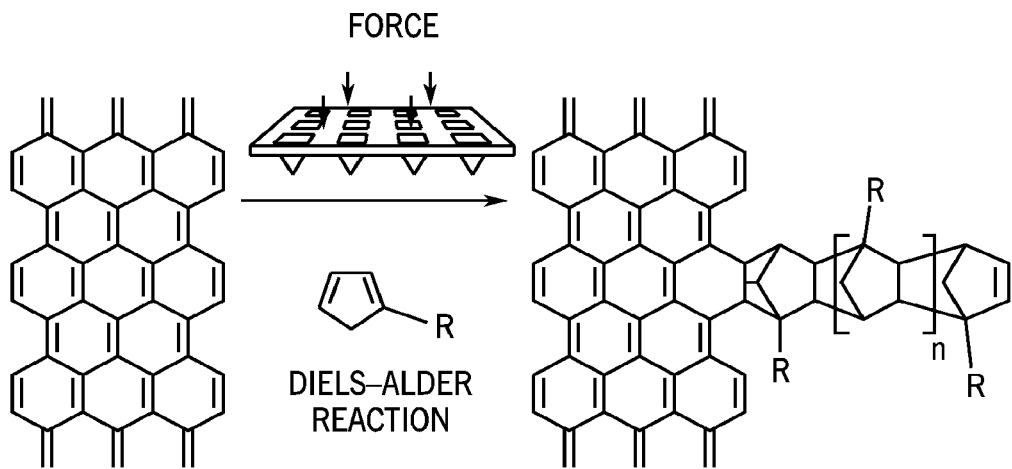
FIG. 19(A) shows a DA obligomerization reaction between functionalized CP and a single layer graphene (SLG) surface.

To further study the reaction between CP and SLG as well as explain the CV and AFM results, DFT calculations were conducted for DA reactions of CP on three representative bonds in a 5×5 graphene model (see FIG. 19(A)). Hydrogen-substituted edges were used, although the nature of the edge is likely complex. The corner bond "a" can be viewed as the joint part of zigzag and armchair edges of graphene. Another periphery bond "b" represents the edges, and the center bond "c" most resembles the pristine graphene interior. All structures were optimized at M06-2X/6-31G(d) level, and single point energy calculations were carried on the optimized structures at M06-2X/6-311G(d,p) level. We report here only the situation of graphene acting as dienophile, and CP as diene. Two more reaction pathways were also calculated but found to be unfavorable.

Computational results see Table 1 of Example 4) show that only reaction at bond "a" is favorable with the reaction enthalpy of −12.6 kcal/mol. Bonds "b" and "c" involve unfavorable, endothermic enthalpies under standard conditions. The bond "c" most resembles the interior of pristine graphene. The thermochemical calculations of single CP on graphene demonstrate that center bonds cannot be functionalized through DA reactions with CPs, and only some special edges, comparable to defect sites, will be reactive. However, once the CP has been attached to the edge positions, it might either activate nearby bonds or itself react. The DA reaction of a second CP on the graphene-CP cycloadduct (functionalized on bond "a") was also calculated (see FIG. 19(B)). Five additional bonds were evaluated ("a", "b", "c", "d", and "e", see FIG. 19(B)). The new reaction enthalpies for the CP addition on bonds "a", "b", and "c" of the graphene-CP cycloadduct (Table 2 of Example 4) are practically unchanged. This clearly indicates that the functionalization at the edge bond "a" does not favor the subsequent CP addition on the graphene lattice. The enthalpies on neighboring bonds "d" and "e" are 0.1 and 32.0 kcal/mol, respectively. Cycloaddition on bond "e" is impossible because of high endothermicity. Bond "d" can be viewed as the edge bond on a 4×4 graphene model and thus possesses a reactivity comparable to bond "a." The enthalpy of −0.1 kcal/mol on bond "d" indicates that the CP group has in fact deactivated its nearby bonds by steric hindrance.

Approximately 20% functionalization was estimated from the CV experiments reported here, while calculations indicate that such a high coverage is not attainable because most of the graphene double bonds are unreactive with CP. How can the differences between experiment and computation be explained? Inspired by recent report of the functionalization of graphene by polymerization we postulate that CP also oligomerizes through DA reactions. FIG. 19(C) shows structures of the graphene-CP cycloadduct and its CP dimerization product. The double bond of the graphene-CP cycloadduct resembles that of norbornene. The reaction enthalpy for the cycloaddition of a second CP is −25.8 kcal/mol. This is significantly more exothermic than any of the reactions of graphene calculated above (the most reactive site on graphene model is bond "a" with ΔH of 12.6 kcal/mol). Once one CP reacts with a reactive edge or defect on graphene, the second CP can react with the norbornene double bond. This can be repeated because CP is well known to dimerize and polymerize through DA reactions. Oligomerization of CP induced by initial Diels-Alder reaction at a graphene defect is preferred over multi-site functionalization. On the basis of the CV characterization, when the average degree of CP oligomerization is 10, the functionalization degree of graphene is ~2%. The length of 10-CP-oligomerized chain is 2.4 nm, which is consistent with the height (~3 nm) measured by AFM. Finally, the dependence of ΔE with scan rate of the CV and the slope of 0.7 in the inset of FIG. 4 can be attributed to hopping of electrons through the fc chains appended to the CP oligomers.

SLG sheets on SiO$_2$ substrates have been patterned covalently with oligomers of organic small molecules through a force-accelerated DA reaction induced on graphene defect and edge sites. The changes in bonding were characterized by Raman microscopy, cyclic voltammetry, and electronic structure calculations, and the results are consistent with micrometer scale features composed of covalently immobilized molecules patterned over large cm² areas. Importantly, these reactions occur at ambient temperature and atmosphere, while accessing one of the most versatile reactions in organic chemistry.

The following non-limiting examples illustrate various aspects of the invention.

EXAMPLES

Example 1: Organic Synthesis and Characterization by NMR and HRMS

All solvents were dried prior to use. All reagents and starting materials were purchased from Aldrich or VWR and used without further purification unless otherwise noted. Aqueous solutions were prepared from nanopure water purified from Milli-Q plus system (Millipore Co.), with a resistivity over 18 MΩ cm$^{-1}$. Compounds 3 and 4 were prepared according to published literature procedures. Thin-layer chromatography was carried out using aluminum sheets precoated with silica gel 60 (EMD 40-60 mm, 230-400 mesh with 254 nm dye). All reactions were carried out under an inert atmosphere of $N_2$ using standard Schlenk techniques or an inert-atmosphere glove box unless otherwise noted. Deuterated solvents were purchased from Cambridge Isotope Laboratories Inc. and used as received. Single layer graphene (SLG) on a silicon water with a 285 nm of thermally grown oxide which is continuous with occasional holes and cracks was purchased from Graphene Supermarket (USA). NMR spectra were obtained on a Bruker AVANCE 400 MHz spectrometer. All chemical shifts were reported in ppm units with reference to the internal solvent peaks for $^1H$ and $^{13}C$ chemical shifts. High-resolution mass spectrometry analyses were carried out on an Agilent 6200 LC/MSD TOF system.

Rhodamine Cyclopentadiene (1).

4-Dimethylaminopyridine (6.8 mg, 0.055 mmol) was added to a stirring solution of 3 (270 mg, 0.55 mmol) and 4 (130 mg, 0.55 mmol) in $CH_2Cl_2$ (2.2 mL) under $N_2$. The solution was stirred for 1 hour before dicyclohexyl carbodiimide (DCC) (135 mg, 0.65 mmol) dissolved in 0.8 mL $CH_2C_2$ was added dropwise to the reaction mixture, which was subsequently stirred for 12 hours, and a white precipitate was observed. The solution was filtered to remove the white precipitate, the precipitate was rinsed with $CH_2Cl_2$ (1.5 mL), the liquid phases were combined, and the solvent was removed in vacuo. The resulting oil product was purified twice by flash chromatography ($SiO_2$:6:100 EtOH:$CH_2Cl_2$) to afford 1 as a red oil (0.17 g, 44%). $^{13}C$ and $^1H$ nuclear magnetic resonance imaging and high resolution mass spectrometry were performed with the following results (see FIGS. 6-8): $^1H$ NMR (400 MHz, $CDCl_3$): δ, 1.30 (m, 22H), 1.73 (d, J=2.4 Hz, 12H), 1.89-1.91 (m, 12H), 2.89 (t, $J_{ab}=J_{bc}$=1.6 Hz, 1H), 2.96 (t, $J_{ab}=J_{bc}$=1.2 Hz, 1H), 3.84 (s, 3H), 4.04 (t, $J_{ab}=J_{bc}$=0.8 Hz, 2H), 4.29 (t, $J_{ab}=J_{bc}$=0.8 Hz, 2H), 6.00-6.03 (m, 0.5H), 6.14-6.17 (m, 0.5H), 6.24-6.27 (m, 0.5H), 6.40-6.47 (m, 1.5H), 7.13 (d, $J_{ab}$=5.2 Hz, 1H), 7.15 (d, $J_{ab}$=5.2 Hz, 1H), 7.24-7.27 (m, 2H), 7.36-7.44 (m, 4H), 7.46-7.52 (m, 2H), 8.45 (t, $J_{ab}=J_{bc}$=13.4 Hz, 2H) ppm. $^{13}C$ NMR (400 MHz, $CDCl_3$): δ 24.79, 25.02, 25.93, 26.42, 27.43, 28.12, 28.18, 28.64, 28.88, 29.47, 29.50, 29.51, 29.52, 29.58, 29.77, 29.87, 30.74, 32.91, 34.00, 41.19, 43.35, 44.88, 48.72, 48.84, 64.44, 105.00, 105.35, 110.77, 110.95, 121.95, 122.07, 125.21, 125.66, 128.88, 130.34, 132.45, 133.54, 134.86, 140.51, 140.67, 142.17, 142.80, 150.83, 173.55, 173.91, 174.05 ppm. HRMS, m/z calculated for $[C_{46}H_{63}N_2O_2]^+$ 675.4890, found 675.4890.

Ferrocene Cyclopentadiene (2).

4-Dimethylaminopyridine (1.7 mg, 0.014 mmol) was added to a stirring solution of ferrocenecarboxylic acid (106 mg, 0.46 mmol) and 4 (109 mg, 0.46 mmol) in THF (1.5 mL) under $N_2$. The solution was stirred for 1 hour before dicyclohexyl carbodiimide (DCC) (114 mg, 0.55 mmol) dissolved in 0.5 mL $CH_2Cl_2$ was added dropwise to the reaction mixture, which was subsequently stirred for 15 hours, and a white precipitate was observed. The solution was filtered to remove the white precipitate, the precipitate was rinsed with $CH_2Cl_2$(1.5 mL), the liquid phase were combined, and the solvent was removed in vacuo. The resulting oil was purified twice by flash chromatography ($SiO_2$:3:1 EtOAc:$CH_2Cl_2$) to afford 2 as a yellow oil (0.055 g, 28%). $^{13}C$ and $^1H$ nuclear magnetic resonance imaging and high resolution mass spectrometry were performed with the following results (see FIGS. 9-11): $^1H$ NMR (400 MHz, $CDCl_3$): δ 1.25-1.37 (m, 12H), 1.69-1.78 (m, 4H), 1.90-1.97 (m, 2H), 2.33-2.42 (m, 2H), 2.88-2.89 (m, 1H), 2.95-2.96 (m, 1H), 3.20-3.21 (m, 2H), 4.20-4.22 (m, 5H), 4.40 (t, $J_{ab}=J_{bc}$=1.8 Hz, 2H), 4.82 (t, $J_{ab}=J_{bc}$=2 Hz, 2H), 6.00-6.01 (m, 0.5H), 6.15-6.17 (m, 0.5H), 6.25-6.29 (m, 0.5H), 6.41-6.45 (m, 1.5H). $^{13}C$ NMR (400 MHz, $CDCl_3$): δ 26.08, 28.93, 29.31, 29.51, 29.60, 29.77, 29.87, 30.73, 41.24, 43.31, 64.35, 69.76, 70.10, 71.21, 125.67, 126.08, 130.36, 132.45, 133.58, 134.84, 171.87 ppm. HRMS, m/z calculated for $[C_{27}H_{36}FeO_2+H]^+$ 449.2143, found 449.2141.

Example 2: Diels-Alder Patterning

Molecules 1 and 2 were synthesized and characterized by $^1H$ NMR, $^{13}C$ NMR, and high-resolution mass spectrometry as described above in Example 1, and all analytical data were consistent with the proposed structures. The 8500 tip arrays with a tip-to-tip spacing of 80 or 160 μm were prepared following previously published literature protocols and are composed of PDMS pyramids mounted onto a glass support (see FIG. 12).

To prepare the pen arrays for inking, they were exposed to $O_2$ plasma (Harrick PDC-001, 30 s, high power) to render the surfaces of the pen-arrays hydrophilic. Subsequently, 4 drops of the ink solution, comprised of 1 (0.8 mg, 1.2 mmol) and PEG (2000 g mol$^{-1}$, 10 mg mL$^{-1}$) in 60:20 THF:$H_2O$ (0.8 mL) that was sonicated to ensure solution homogeneity, were spin coated (2000 rpm, 2 min) onto the pen array. The inking of the array with 1 was observed using fluorescence microscopy (Nikon Eclipse Ti, $\lambda_{ex}$=532-587 nm, $\lambda_{obs}$=608-683 nm). A Park XE-150 scanning probe microscope equipped with a PPL head (Park Systems Corp.), custom lithography software, and an environmental chamber capable of controlling humidity were used for writing at a humidity of 78%-83% at room temperature. The tip array was leveled by optical methods or force methods with respect to the substrate surface using an xy tilting stage. The inked tips were mounted onto an atomic force microscope (AFM) and 2×3 dot arrays under the same Z extension step (18 steps) with dwell times ranging from 30 to 15 min were patterned (30, 27, 24, 21, 18, 15 min). The SLG was washed immediately with EtOH and $H_2O$. Following washing, no fluorescent image could be seen from the fluorescence microscope. In the control experiment, PEG (2000 g mol$^{-1}$, 10 mg mL$^{-1}$) was deposited onto SLG following identical procedure described above. The sample was immediately washed with 5 mL EtOH and 5 mL $H_2O$.

To induce the Diels-Alder reaction between 1 and the SLG surface, 1 (0.8 mg, 1.2 mmol) and poly(ethylene glycol) (PEG) (2000 g mol$^{-1}$, 10 mg ml$^{-1}$) in 0.8 mL 60:20

THF:H2O, which was sonicated to ensure solution homogeneity, were spin coated (2000 rpm, 2 min) onto a tip array. The PEG matrix that encapsulates the cyclopentadienes ensures even distribution across the tip array, and in the case of Polymer Pen Lithography, transport from the tips to a surface is predictable and reproducible. The tips were then mounted onto the z-piezo of an AFM that was specially equipped with an apparatus to hold the tip arrays, an environmental chamber to regulate the humidity, and customized lithography software to control the position, force, and dwell-time of the tips. A 2×3 pattern of 1 with feature-to-feature spacing of 20 μm was patterned by each tip in the array by pushing the tips into the SLG surface (SLG on 285 nm $SiO_2$) at times ranging from 15-30 min and a force of ~100 mN at each spot. The transfer of small molecule/PEG mixture to the surface was confirmed by light microscopy (see FIG. 2(A)), and the 2×3 PEG/cyclopentadiene patterns and the approach dot used to level the tip array with respect to the surface are clearly visible.

After washing the surfaces with EtOH and $H_2O$ to remove unbound 1 and PEG, the surface bonding was analyzed by Raman microscopy (Renishaw inVia, 633 nm excitation). A Raman map of the surface that was obtained following force accelerated printing of 1 revealed a 2×3 pattern of features where $I_D$ was elevated significantly compared to surrounding areas (see FIGS. 2(B) and 13). The dimensions and feature sizes of these 2×3 pattern with 20 μm spacing between features matched with the pattern of features printed by the pen array. The elevated $I_D$ was observed at all points where the tips were pressed into the surface for all dwell times. Importantly, control experiments where 1 was not present in the ink mixture or where 1 was present but force was not applied to the surface upon ink transfer did not produce similar patterns or significantly elevated $I_D/I_G$ in the Raman maps, confirming that the diene is necessary for changes in bonding to occur. The Raman spectra associated with different points on this map further confirmed that the changes in bonding were produced because of the occurrence of localized Diels-Alder reactions (see FIGS. 3(A)-3(E)). A Raman spectrum taken at a point where the tips were pressed into the surface had peaks corresponding to the SLG D-band and 1, as well as an increased $I_D/I_G$ value of 0.95, compared to 0.49 for the unaltered surface, 0.46 where the tips had been pressed into the surface in the absence of 1, and 0.39 for the original SLG surface. The changes in the $I_D/I_G$ in the Raman maps confirm changes in bonding from $sp^2$ to $sp^3$ and are consistent with those previously observed for Diels-Alder reactions on the surface, and the control experiments confirm that the changes in the spectrum only occur under conditions where the Diels-Alder reaction can proceed. Unlike cycloadditions under pressure, where rate accelerations arise because of the negative activation volume, it is conceivable that under force, rate acceleration may also arise because of the distortions of π-bonds of SLG upon the application of force that increase their reactivity.

Raman spectra were acquired with 5 s exposure time and 20 accumulation in an inVia Raman microscope using 633 nm laser while the Raman maps were recorded with 1 s exposure time and 3 accumulation by raster scanning with a two-dimensional stage having a step size of 3 μm. The grating and laser power for both raman mapping and spectra are 1800 l/mm and 50%. The ratio of the integrated area between D- (1324 $cm^{-1}$) and G-band (1584 $cm^{-1}$) ($I_D/I_G$) in Raman spectra was employed to confirm the success of Diels Alder reaction on SLG. In FIGS. 3(a)-3(e), it was observed that the dye peak (1590 $cm^{-1}$) overlapped with the G peak (1584 $cm^{-1}$) on SLG. The ratio between the integration area of that dye peak at 1590 $cm^{-1}$ and 1385 $cm^{-1}$ is approximately 1.5 based on FIG. 3(A) and therefore in FIG. 3(B), we subtract the integrated area of the dye peak (1590 $cm^{-1}$) based on the area of the dye peak (1385 $cm^{-1}$) from the total integrated area of peak at around 1584 $cm^{-1}$. The measured $I_D/I_G$ is 0.948 for 1-patterned SLG (see FIG. 3(B)) while the $I_D/I_G$ is 0.499 for non-patterned spot on the same SLG (FIG. 3(C)). The $I_D/I_G$ value (0.460) for control sample (see FIG. 3(D)) is similar to that (0.39) for pure SLG (see FIG. 3(E)). The increased $I_D/I_G$ value in the spectrum of the spot patterned by 1 confirms the Diels Alder reaction on the SLG. While not limiting the scope or meaning of the invention, in other calculations which were performed later, the values for the above are, respectively: 0.56; 0.16; 0.14 and 0.17.

Example 3: Cyclic Voltammetry Characterization

Figure 4:
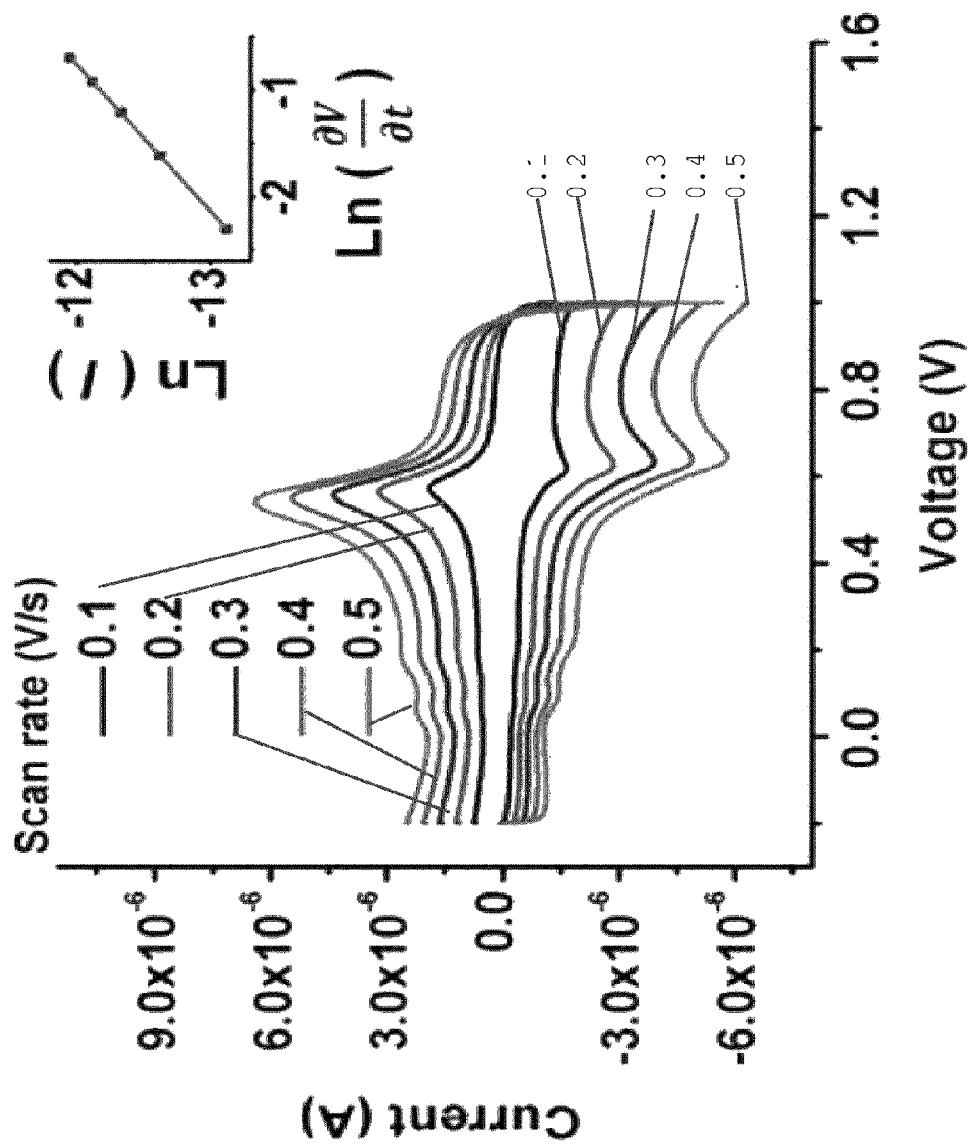
FIG. 4 is a cyclic voltammetry (CV) characterization of the SLG patterned with 2 using a Pt counter electrode and Ag/AgCl reference electrode in 0.1M $HClO_4$ electrolyte solution, showing the linear relationship between scan rate and current and indicating that 2 is surface immobilized.
Figure 5:
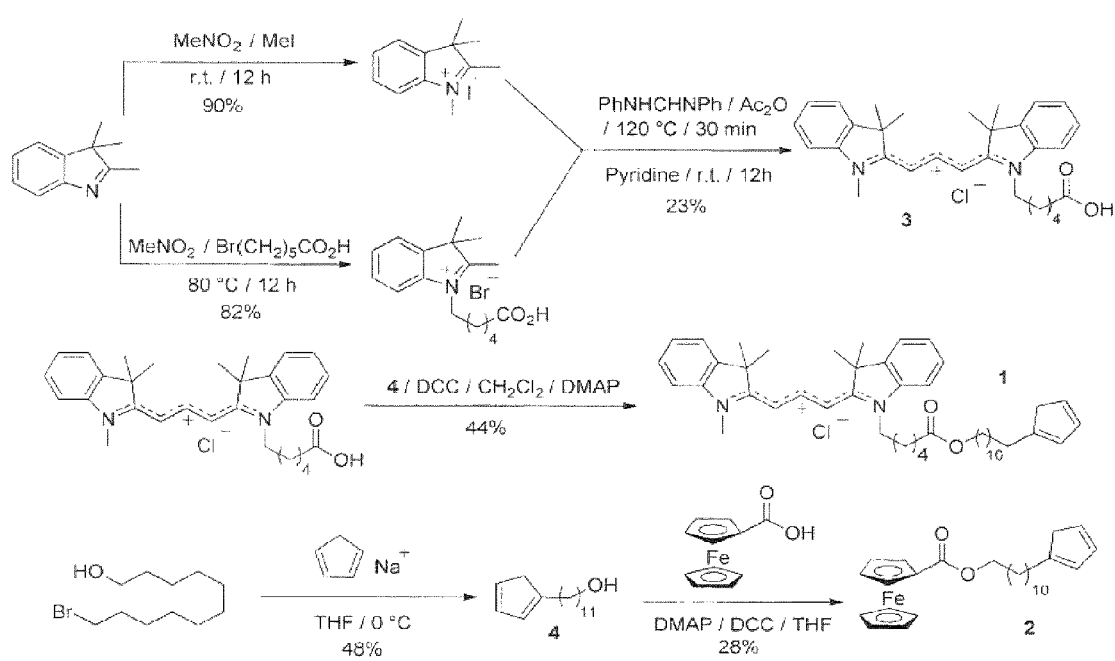
FIG. 5 is a schematic diagram showing preparation of ink molecules 1 and 2.
Figure 6:
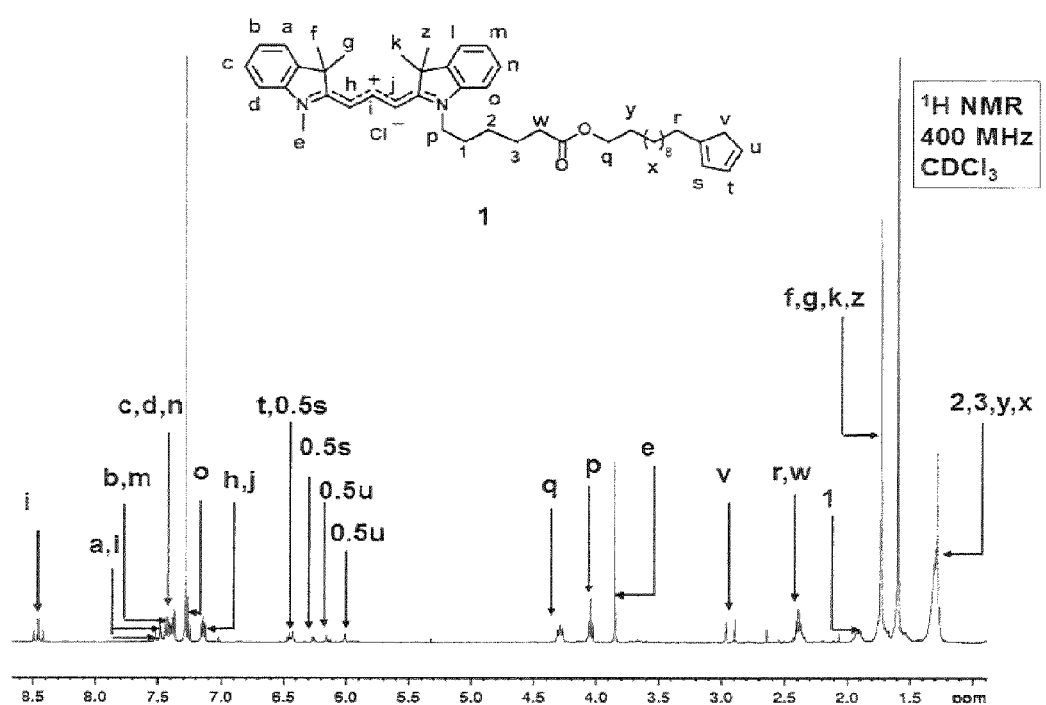
FIG. 6 shows the $^1H$ nuclear magnetic resonance spectrum of 1.
Figure 7:
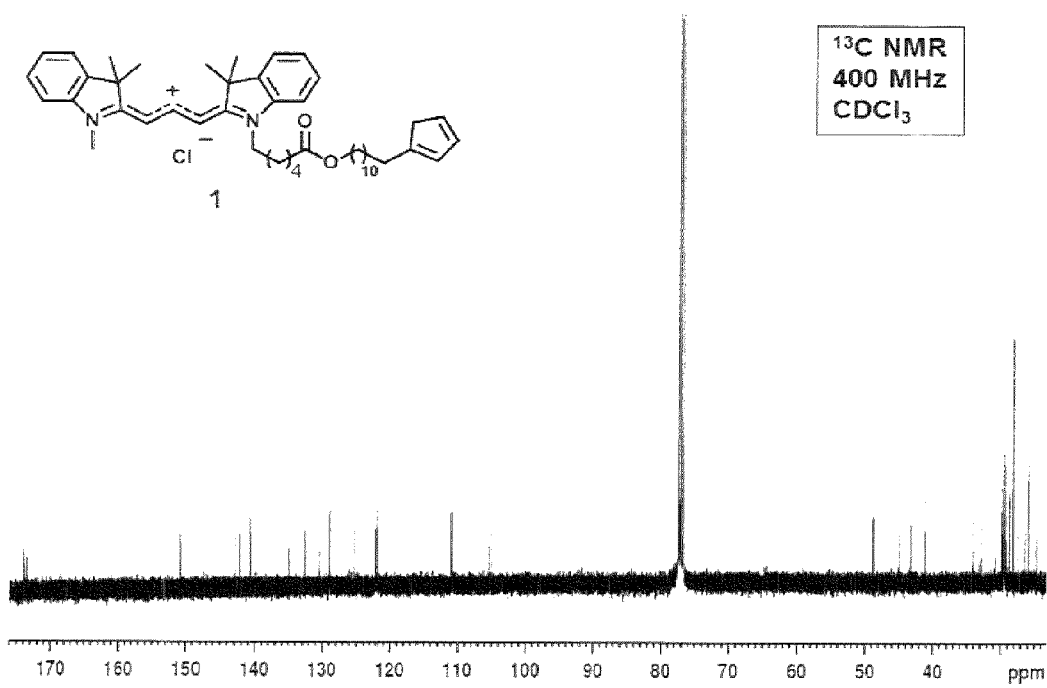
FIG. 7 shows the $^{13}$C NMR spectrum of 1.
Figure 8:
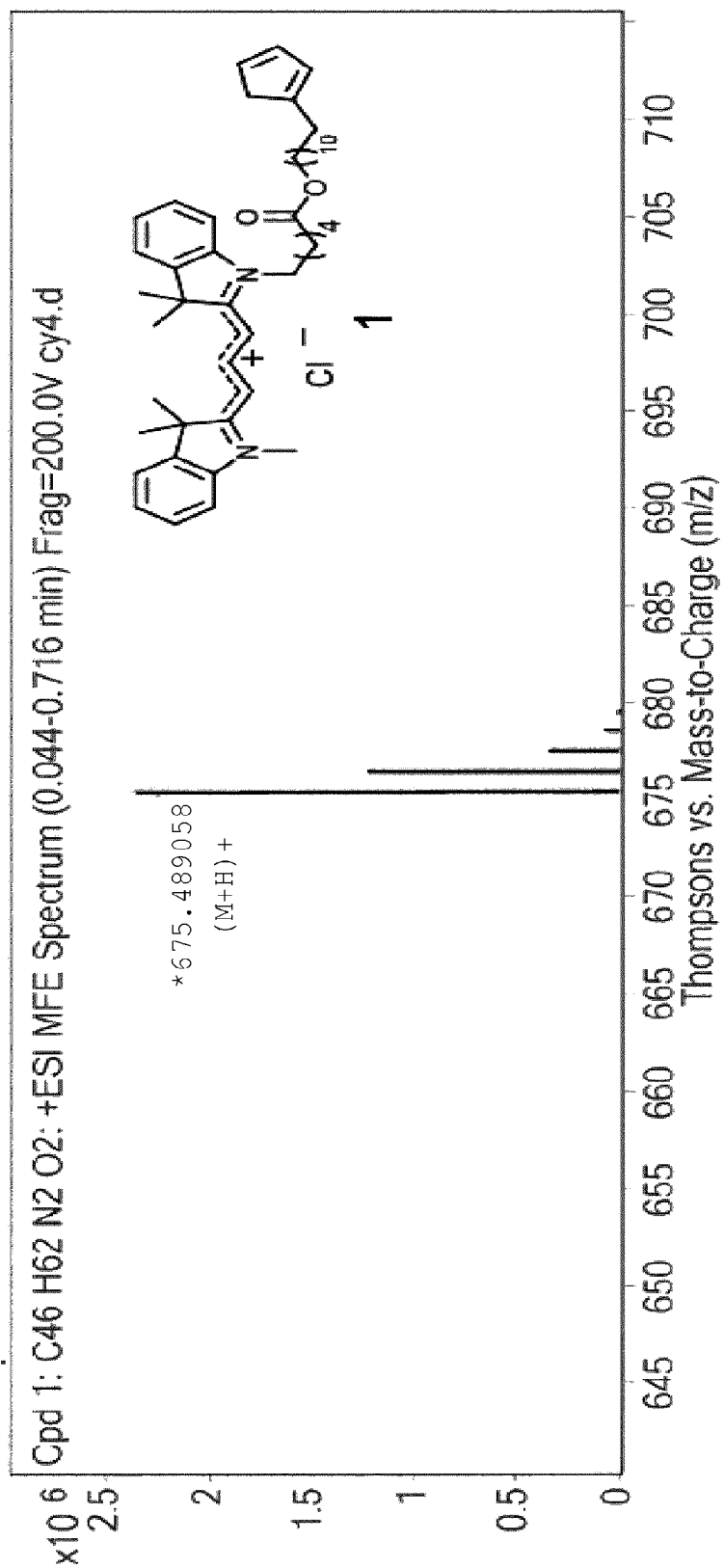
FIG. 8 shows the high resolution mass spectrum of 1.
Figure 9:
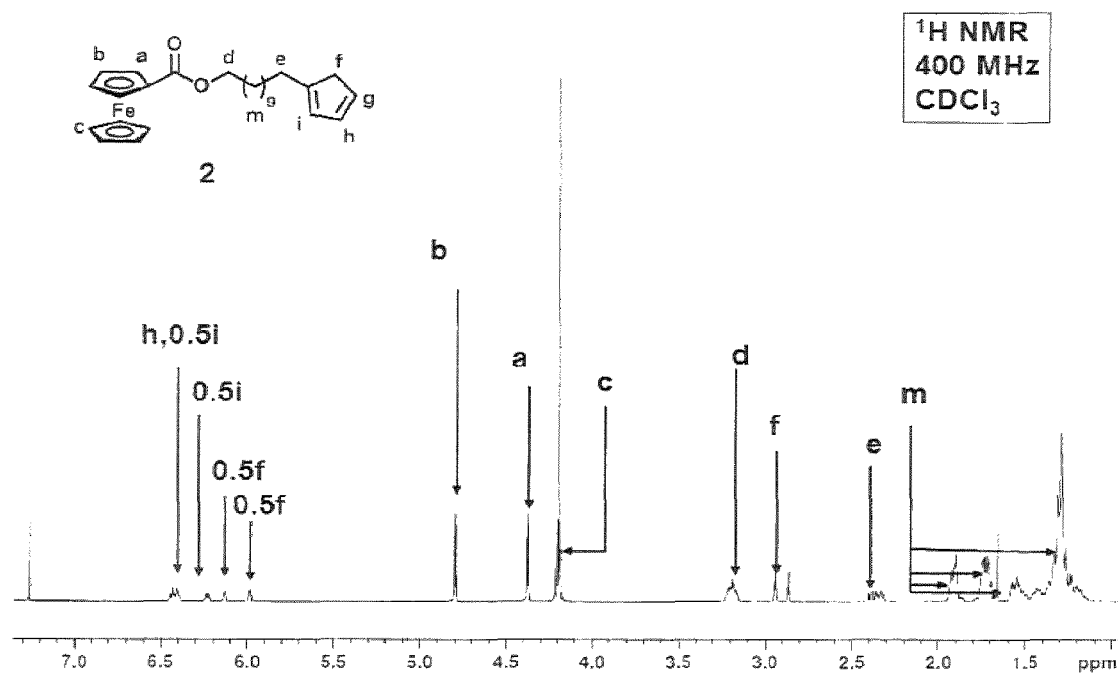
FIG. 9 shows the $^1$H NMR spectrum of 2.
Figure 10:
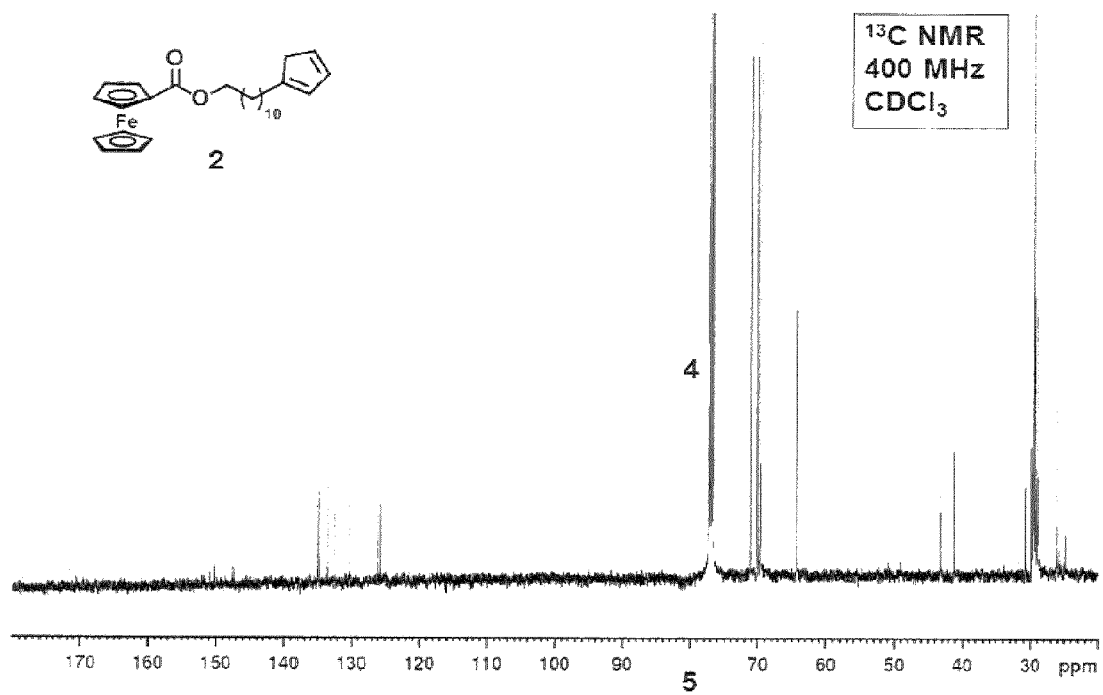
FIG. 10 shows the $^{13}$C NMR spectrum of 2.
Figure 11:
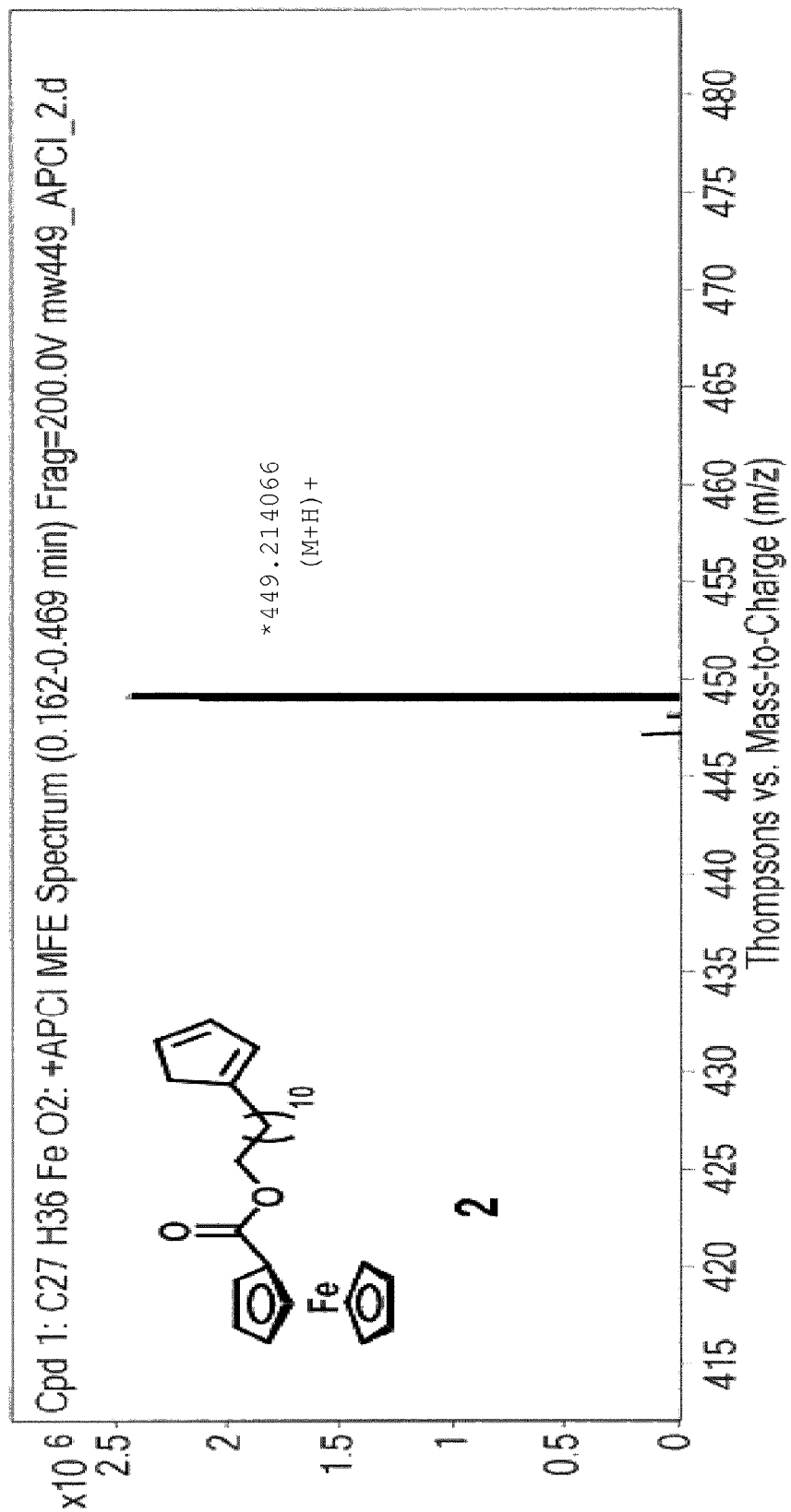
FIG. 11 shows the high resolution mass spectrum of 2.
Figure 12:
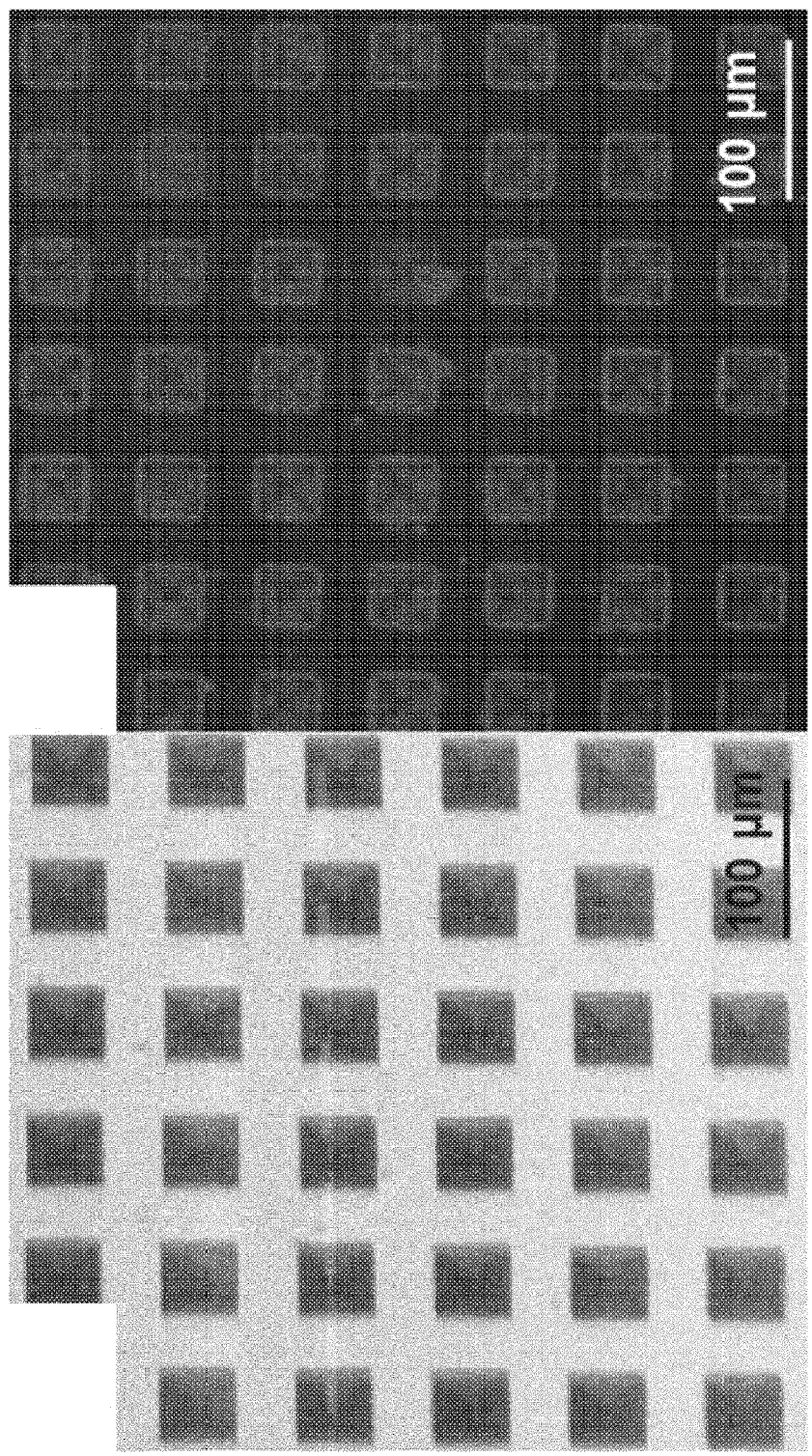
FIG. 12(A) shows an optical microscopy image of a 8500-pen tip array with tip-to-tip spacing of 80 μm.
FIG. 12(B) fluorescence microscope (Nikon Eclipse Ti, $\lambda_{ex}$=532-587 nm, $\lambda_{obs}$=608-683 nm) image of 8500-pen tip array inked with 1 ($\lambda_{ex}$=550 nm) and PEG.
Figure 13:
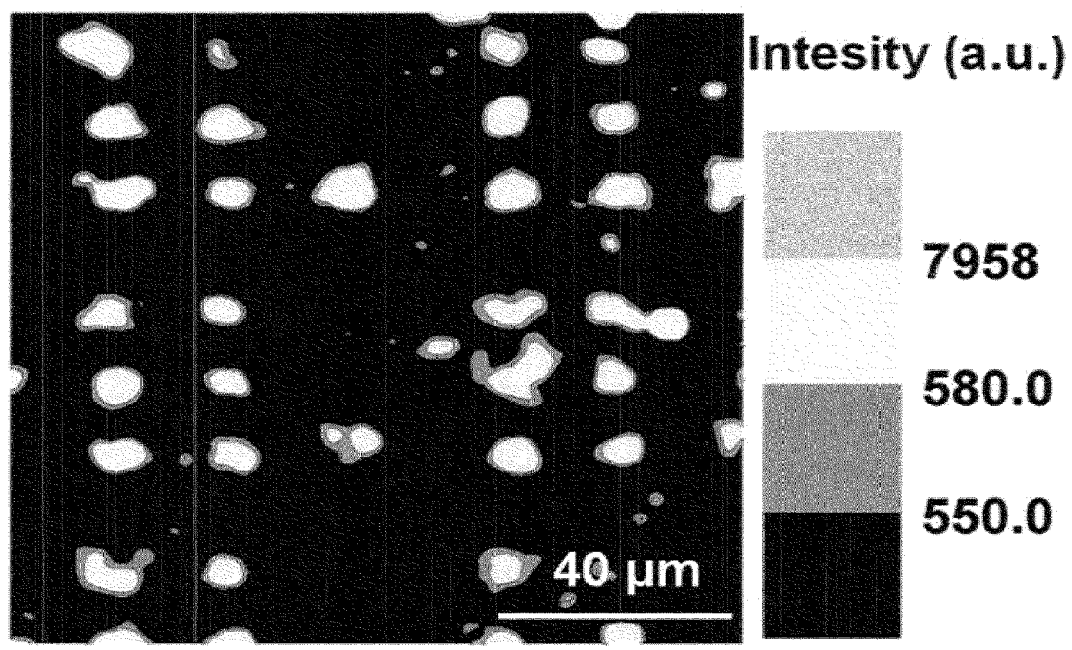
FIG. 13 shows a Raman mapping image of 1 covalently immobilized on SLG.
Figure 14A:
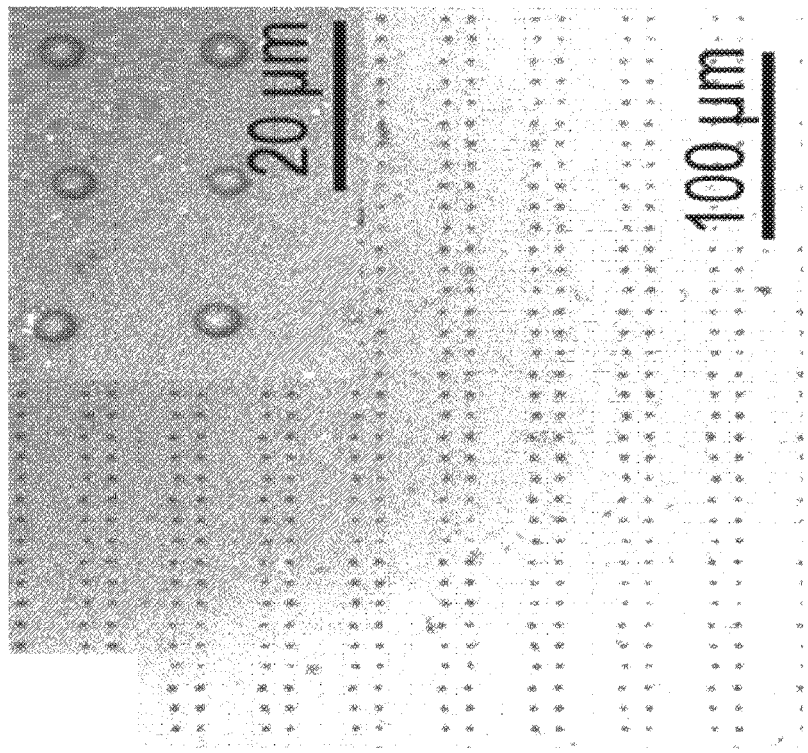
FIG. 14(A) shows Cyclic Voltammetry (CV) characterization of SLG using a Pt counter electrode and Ag/AgCl/1M KCl reference electrode in 0.1M HClO$_4$(aq)
Figure 16:
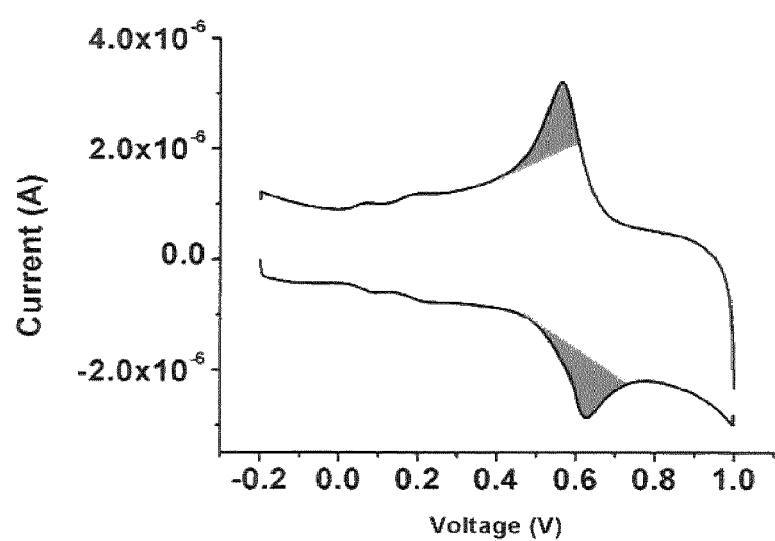
FIG. 16 shows cyclic voltammograms (0.1M HClO$_4$ electrolyte solution (aq), Ag/AgCl reference electrode, Pt counter electrode, at 0.2 V/s scan rate) of the 2 bearing SLG.

Electrochemically active cyclopentadiene 2 was patterned onto SLG following a similar protocol described above, and the immobilization density of 2 on the SLG surface was analyzed by cyclic voltammetry (CV) as shown in FIGS. 4, 14(A) and 16.

Figure 14B:
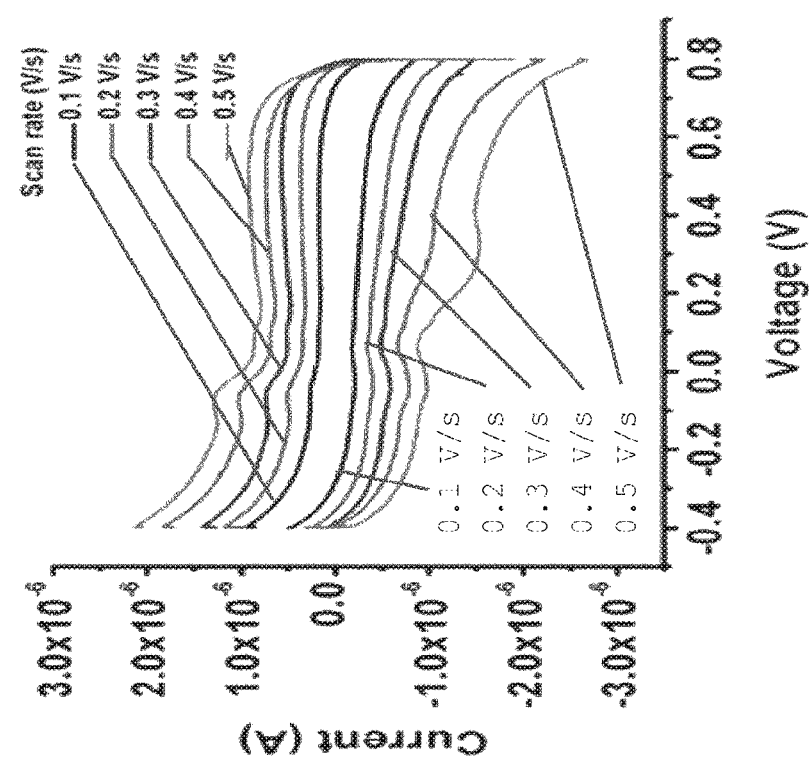
FIG. 14(B) shows an optical microscope image (10× magnification) of 2×3 dot arrays of ink mixture containing 2 and PEG with the same dwell times (30 min) and patterned by each pen in the tip array, with the inset showing the image at 50× magnification.

2×3 dot arrays of ink mixture containing 2 and PEG with same dwell times (30 min) were patterned by each pen in the tip array (see FIG. 14(B)). Cyclic voltammetry (CV) was carried out with a Pt counter electrode, a glass frit-isolated Ag/AgCl reference electrode and the SLG surfaces as the working electrode. The SLG was immersed in a beaker containing 10 mL 0.1M $HClO_4$ (aq) electrolyte solution. An electrochemical workstation (CFI Instruments, Inc., CHI 440) was used to control the potential and convert the cell current to a potential signal. A Tektronix TDS 520 digital oscilloscope recorded the current response signal from the potentiostat while a Wavetek 395 function generator generated potential program signal. All measurements were conducted at room temperature. The cyclic voltammetry of pure SLG was measured before printing and small peaks between 0-0.2 v are present (see FIG. 14(A)).

As shown in FIG. 14(B) each tip in the pen array produced a 2×3 dot pattern over the 1 $cm^2$ area covered by the tip array with a dwell time of 30 s at each spot, and ink deposition was confirmed by optical microscopy with an average feature edge length of 7.1 μm and area of 50.4 $μm^2$. Following washing of the surface with EtOH and $H_2O$ to remove the PEG and unreacted 2, CV was carried using an Ag/AgCl reference electrode, a Pt counter electrode, and the patterned SLG as the working electrode. A strong redox peak at E°=590 mV (vs. Ag/AgCl) confirmed the presence of the ferrocene (fc)/ferrocenium ($fc^+$) reversible redox couple from 2 (see FIG. 4), which is shifted anodically compared to fc because of the ester linking the fc to the cyclopentadiene. The linear relationship between peak current and scan rate confirmed that 2 is immobilized on the SLG surface, but that the localized changes in bonding from $sp^2$ to $sp^3$ do not prevent conduction through the SLG. However, the difference between oxidation and reduction peaks may indicate an increase in resistance upon changes in chemical bonding from $sp^2$ to $sp^3$. The surface density of fc within each feature, $\Gamma_{fc}$, was determined from the CV measurements using Equation 3.

$$\Gamma_{fc} = Q_{fc}/neA \quad (3)$$

Where $Q_{fc}$ is the total charge passed in the redox reaction, n is the change of the oxidation number of the redox-active species (n=1 for fc). A is the surface area of the patterned features on the working Au electrode, and e is the electron charge. A $\Gamma_{fc}$ of $(5.34\pm0.76)\times10^{14}$ cm$^{-2}$ was obtained. If we consider the density oft-bonds on the graphene surface, this number corresponds to approximately 29% of bond functionalization. Control experiments where 2 was deposited without force did not result in any observable current corresponding to the fc/fc$^+$ redox couple after washing, confirming that force is necessary to induce the Diets Alder reaction under these conditions.

Figure 15B:
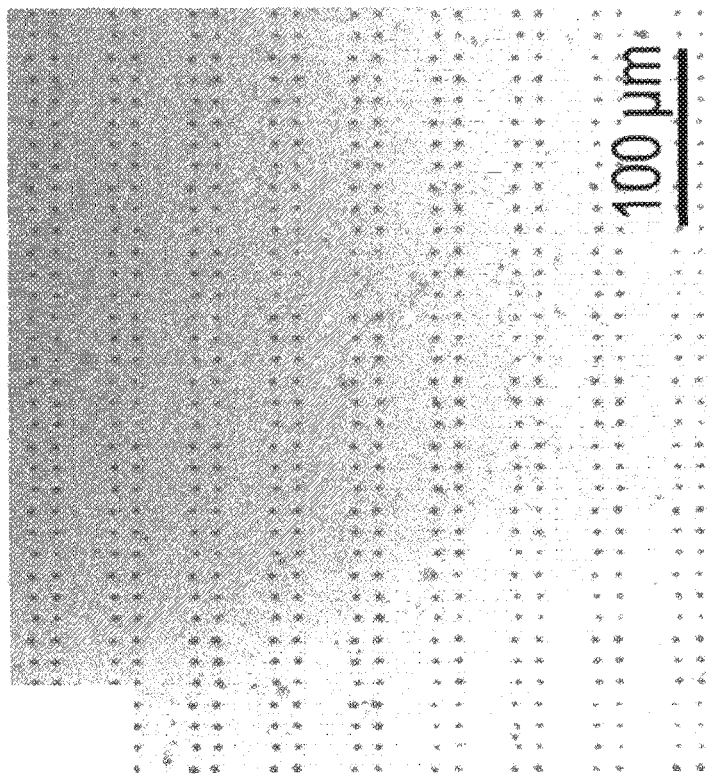
FIG. 15(B) a Cyclic Voltammetry (CV) characterization of SLG surface in the control experiment using a Pt counter electrode and Ag/AgCl/1M KCl reference electrode in 0.1M HClO$_4$(aq)
Figure 15A:
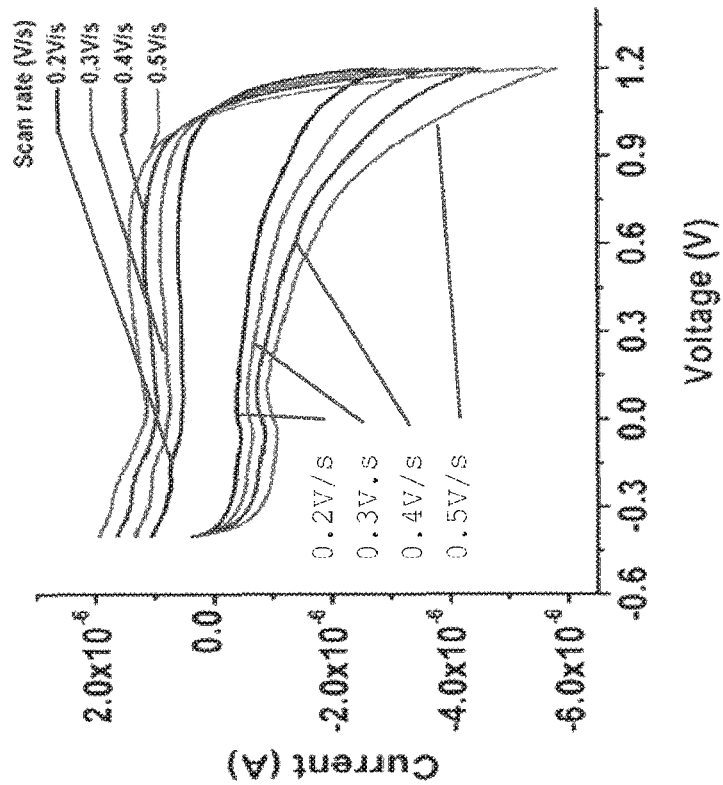
FIG. 15(A) shows an optical image of ink 2 and PEG on SLG in the control experiment.

To confirm the Diels-Alder reaction on SLG was catalyzed by force, PEG (2000 g mol$^{-1}$, 1.0 mg mL$^{-1}$) and as shown in FIG. 15(A), ink 2 (0.54 mg, 1.5 mM) in 60:20 THF:H$_2$O (0.8 mL) was deposited onto the SLG following identical procedure described above but with the z extension of 2 steps (1.9 mN). The sample was immediately washed with 5 mL EtOH and 5 mL H$_2$O after printing. The surface was then dried in a N$_2$ stream and subsequently characterized by cyclic voltammetry see FIG. 15(B)). No peaks corresponding to the fc/fc$^+$ redox couple were observed.

The cover density of fc, $\Gamma_{fc}$, was calculated using Eq. 2

$$\Gamma_{fc}=Q_{fc}/neA \quad (2)$$

$Q_{fc}$, the total charge passed in the redox reaction, was calculated by dividing the integral of the redox peak by the corresponding scan rate. The $Q_{fc}$ for the deposited fc on SLG was $(1.56\pm0.05)\times10^{-6}$ C. A, the surface area of the working electrode, was calculated by the total area covered by 2. For the PPL deposited 2, A=0.0176 cm$^2$ based on the feature edge length (7.10 μm) measured by optical microscope before washing. So the cover density of 2 within the features of the array was calculated to be $(5.54\pm0.78)\times$cm$^{-2}$. However based on the relationship between force and feature size, the calculated feature length for each spot in FIG. 2(A) should be 7.68 μm and therefore A=0.0206 cm$^2$. In this case the cover density of 2 within the features of the array was calculated to be $(4.73\pm0.67)\times10^{14}$ cm$^{-2}$.

The approximate density of reactive π bond ($\Gamma_\pi$) on the single layer (SLG), which acts as dienophile in the Diets Alder reaction, was calculated. In the ideal structure below, every ring on SLG except the edges has one reactive Π bond. For SLG with an area of 0.372 cm$^{-2}$, the number of rings (N) was calculated to be approximately $7.11\times10^{14}$. Therefore $\Gamma_\Pi$ was acquired using Eq. 4

$$\Gamma_\Pi=N/0.372=7.11\times10^{14}/0.372=1.9\times10^{15}\ \text{cm}^{-2} \quad (4)$$

Example 4; Computations

All calculations were performed with the Gaussian 09 program package. The geometry optimization of all the minima and transition states involved was carried out at the M06-2X level of theory with the 6-31G(d) basis set. The vibrational frequencies were computed at the same level to check whether each optimized structure is an energy minimum or a transition state and to evaluate its zero-point vibration energy (ZPVE) and thermal corrections at 298 K. A quasiharmonic correction was applied during the entropy calculation by setting all positive frequencies that are less than 100 cm$^{-1}$ to 100 cm$^{-1}$. Single point energy calculations were carried on the optimized structures at the M06-2X/6-311G(d,p) level.

DFT calculations were conducted for Diels-Alder reactions of CP on three representative bonds in the 5×5 graphene model as shown in FIG. 19a. Table 1 shows the calculated reaction enthalpies (ΔH) and Gibbs free energies (ΔG). The free energy term (ΔG) is less favorable due to the entropy contribution (ΔG=ΔH−TΔS, −TΔS is positive). Recently, it was reported that the entropy contribution is small (about 2-3 kcal/mol) from calculations on free energies of the non-covalent association of graphene with small organic molecules. The actual −TΔS values for the Diels-Alder reactions studied here are likely to be around 5-10 kcal/mol. We use enthalpy of reaction to evaluate the feasibility of reactions, while Gibbs free energies from calculations are given for reference, but are probably too high by 5-10 kcal/mol.

TABLE 1

Energies of Diels-Alder reactions of bonds a, b, and c with CP; energies in kcal/mol.

| | bond | | |
|---|---|---|---|
| | a | b | c |
| ΔH | −12.6 | 4.3 | 34.2 |
| ΔG | 3.2 | 20.1 | 50.6 |

Figure 19B:
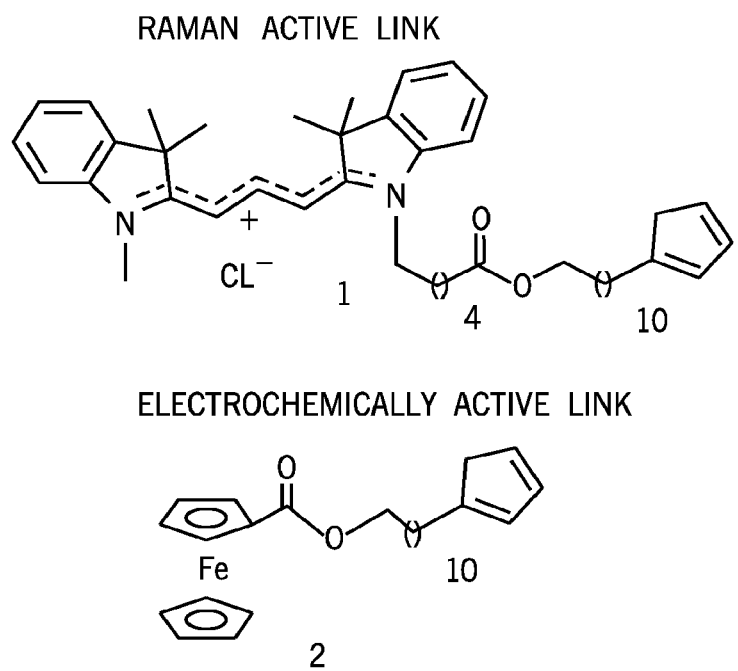
FIG. 19(B) shows Cy3-containing Raman active 1 and ferrocene-containing electrochemically active 2 ink molecules used to confirm force-accelerated patterning.
Figure 19C:
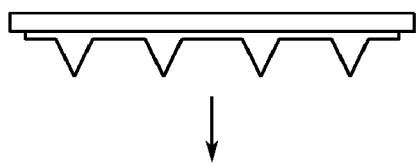
FIG. 19(C) shows an elastomeric tip-array.
Figure 20:
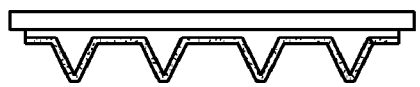
FIG. 20 shows the Diels-Alder reactions of three representative bonds (1, 2, and 3) with CP; graphene functions as the 4 π component and CP functions as the 2 π component.
Figure 19D:
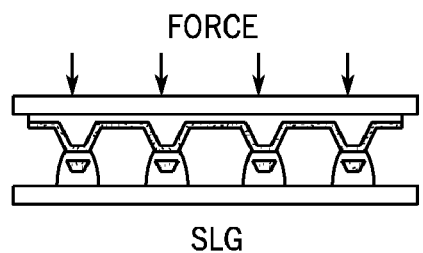
FIG. 19(D) shows the tip-array coated with an ink mixture (red or "r") consisting of a CP and poly(ethylene glycol) (PEG)
Figure 19E:
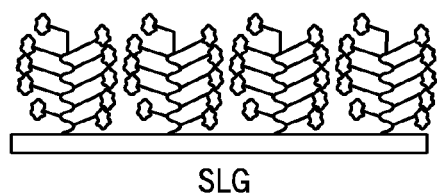
FIG. 19(E) shows the inked tip array being pushed into the SLG surface.
Figure 19F:
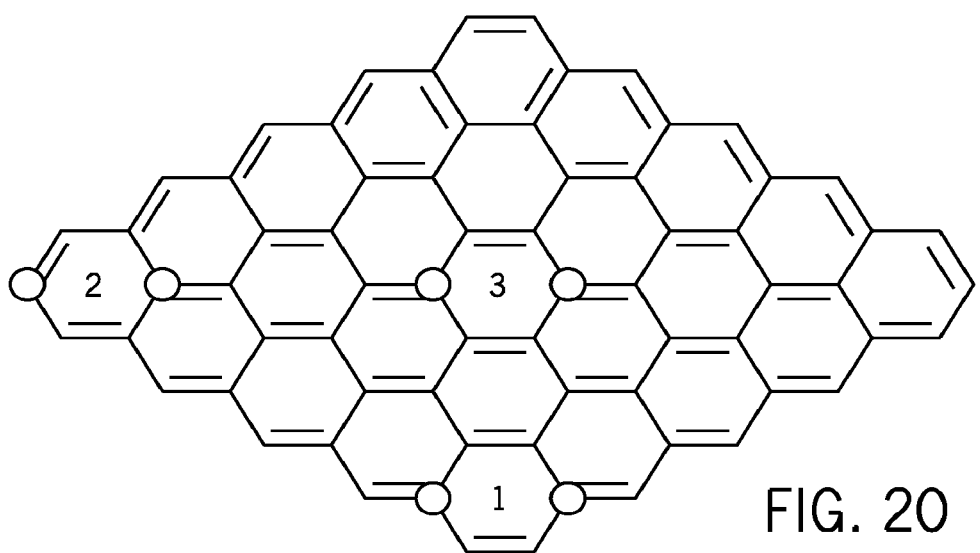
FIG. 19(F) shows following rinsing of the surface to remove the PG and excess CP, only the covalently immobilized. molecules remaining on the surface.

Table 2 shows the reaction energies for the second CP addition as shown in FIG. 19(B). Comparing a, b, and c bonds from Tables 1 and 2, their energies are practically the same. This indicates that the functionalization at the edge bond "a" has no effect on bonds far away. The enthalpies on neighboring bonds "d" and "e" are −0.1 and 32.0 kcal/mol, respectively. Cycloaddition on bond "e" is impossible due to high endothermicity. Bond "d" can be viewed as the edge bond on a 4×4 graphene model and thus possesses a reactivity comparable to "a". The enthalpy of −0.1 kcal/mol on bond "d" indicates that the CP group has in fact deactivated its nearby bonds by steric hindrance.

TABLE 2

Energies of Diels-Alder reactions of bonds a-e of the graphene-CP cycloadduct with the second CP; energies in kcal/mol.

| | bond | | | | |
|---|---|---|---|---|---|
| | a | b | c | d | e |
| ΔH | −12.6 | 3.9 | 34.2 | −0.1 | 32.0 |
| ΔG | 3.3 | 19.8 | 50.5 | 16.5 | 48.2 |

Study on Diels-Alder reactions of graphene as diene and cyclopentadiene as dienophile. These reactions (see FIG. 20) are all extremely endothermic (see Table 3). It is believed that there is no possibility for the DA reaction of CP with graphene as diene.

TABLE 3

Energies of Diels-Alder reactions of bonds 1, 2, and 3 with CP; energies in kcal/mol.

| | bond | | |
|---|---|---|---|
| | 1 | 2 | 3 |
| ΔH | 72.5 | 31.9 | 53.5 |
| ΔG | 88.0 | 47.9 | 69.6 |

Study on Alder Ene Reactions of Graphene and Cyclopentadiene.

Similar to the DA reaction described in the main text, only the reaction at the edge bond "a" gives favorable reaction enthalpy (FIG. 19(B) and Table 4). Bonds "b" and "c" are not reactive according to the calculation (see Table 4).

TABLE 4

Energies of Alder ene reactions of bonds a, b, and c with CP; energies in kcal/mol.

| | bond | | |
|---|---|---|---|
| | a | b | c |
| ΔH | −9.4 | 8.3 | 46.3 |
| ΔG | 5.0 | 22.6 | 61.4 |

Figure 21:
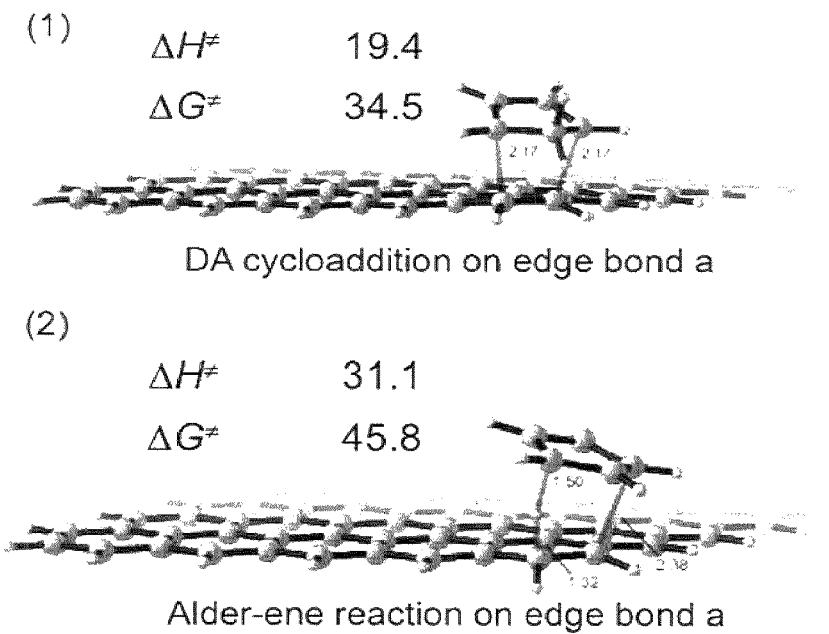
FIG. 21 shows transition states of (1) DA reaction (Graphene functions as the 2 π component) and (2) Alderene reaction on edge bond "a"; energies are in kcal/mol.

As shown in FIG. 21, the transition state calculations further demonstrate that the DA reaction path is favored over the Alder ene reaction due to a significantly smaller barrier (19.4 versus 31.1 kcal/mol).

Figure 22:
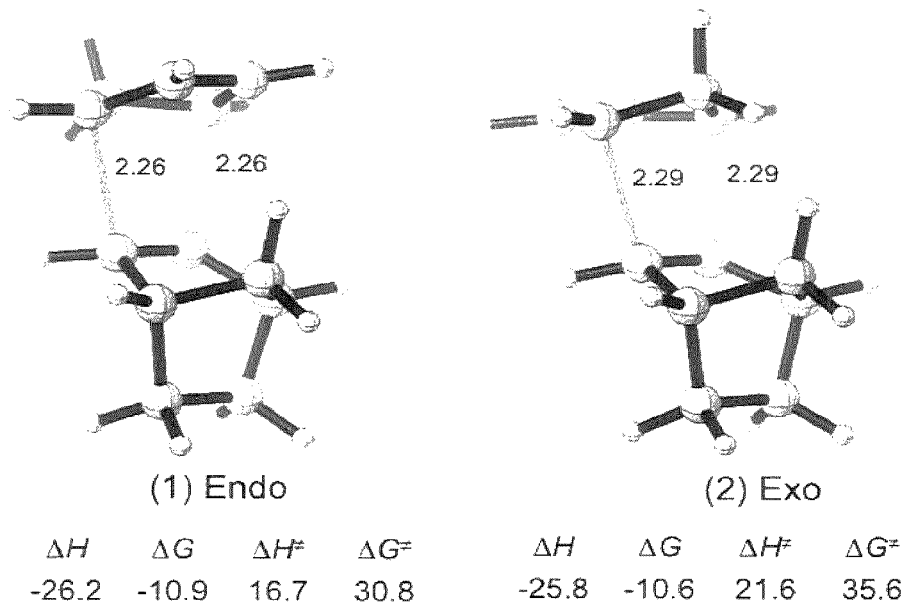
FIG. 22 shows transition states of the Diels-Alder reaction of CP with norbornene Endo and (2) Exo; energies are in kcal/mol.
Figure 23:
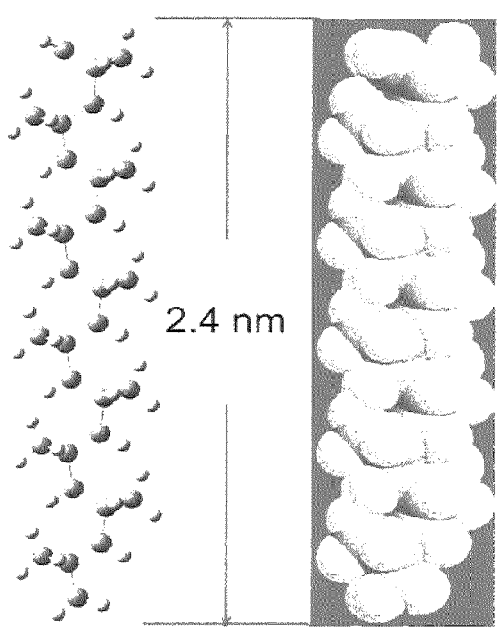
FIG. 23 shows the structure of 10-CP-oligomerized chain with a length of 2.4 nm; optimized at the M06-2X/6-31G(d) level.

Two stereoisomers (Endo and Exo) can be formed by the DA reaction of CP with the graphene-CP cycloadduct (See FIG. 19(C)). Here norbornene is used as a model to assess the two isomers (FIG. 22). Their reaction enthalpies and free energies have minor differences. Endo product is slightly preferred by 0.4 kcal/mol in terms of enthalpy, but the reaction barrier to form endo product is 16.7 kcal/mol, about 5 kcal/mol lower than that of exo (see FIG. 22). Therefore, it is proposed that the polymerizations of CPs on graphene are all in the endo form. The length of 10-CP-oligomerized chain is 2.4 nm as shown in FIG. 23.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of selectively locally increasing the bandgap of a graphene sample comprising the steps of:
   (a) coating an elastomeric tip array with an ink mixture comprising a second reactive element consisting of or bound to a soft matter element; and
   (b) inducing a localized force-accelerated reaction between a first reactive element positioned on a basal plane of a single layer graphene sample and the second reactive element by mechanical application of the elastomeric tip array to the graphene basal plane, thereby forming a covalent bond between the first and second reactive elements; and
   wherein the bandgap is increased in those locations on the basal plane of the graphene with the covalent bond between the first and second reactive elements.

2. The method of claim 1, wherein the force-accelerated reaction is a cycloaddition.

3. The method of claim 1, wherein the cycloaddition is selected from the group consisting of Diels-Alder, a 1-3 dipolar cycloaddition, a [4+2] cycloaddition of cations and anions, a cycloaddition involving more than six electrons, a photochemical cycloaddition, and a stepwise cycloaddition.

4. The method of claim 1, wherein the first reactive element is a dienophile.

5. The method of claim 4, wherein the second reactive element is a diene.

6. The method of claim 5, wherein the dienophile is a localized pi-bond of the single layer graphene sample.

7. The method of claim 6, wherein the diene is rhodamine cyclopentadiene or ferrocene cyclopentadiene.

8. The method of claim 1, wherein the force-accelerated reaction results in a cyclohexane formation covalently bonding the first and second reactive elements.

9. The method of claim 1, wherein the soft matter is selected from the group consisting of nanoparticles, organics, biologicals, polymers, proteins, sugars, oligonucleotides, peptides, and antibodies.

10. The method of claim 1, wherein mechanical application of the elastomeric tip array to the graphene basal plane is for a dwell time of between 15 minutes and 30 minutes.

* * * * *